US010616954B2

(12) United States Patent  
Belongia et al.

(10) Patent No.: US 10,616,954 B2  
(45) Date of Patent: Apr. 7, 2020

(54) ELECTRICAL BARRIER FOR WAX WARMER

(71) Applicant: S. C. Johnson & Son, Inc., Racine, WI (US)

(72) Inventors: David C. Belongia, Green Valley, AZ (US); Dennis J. Beaumont, Libertyville, IL (US); Michael J. Goodrich, Oak Park, IL (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 15/784,427

(22) Filed: Oct. 16, 2017

(65) Prior Publication Data

US 2018/0042070 A1 Feb. 8, 2018

Related U.S. Application Data

(63) Continuation-in-part of application No. 15/595,645, filed on May 15, 2017, now Pat. No. 10,225,885, (Continued)

(51) Int. Cl.
*H05B 3/00* (2006.01)
*A61L 9/03* (2006.01)
(Continued)

(52) U.S. Cl.
CPC ............. *H05B 1/0252* (2013.01); *A61L 9/03* (2013.01); *H05B 3/0052* (2013.01); *H05B 3/26* (2013.01); *A61L 2209/135* (2013.01); *H05B 2203/02* (2013.01); *H05B 2203/021* (2013.01); *H05B 2203/022* (2013.01)

(58) Field of Classification Search
CPC ... H05B 3/00; A61L 9/03; A61L 9/035; A61L 9/037; F24F 11/00
USPC ......... 392/385–386, 391–398; 219/429–432; 239/34–60
See application file for complete search history.

(56) References Cited

U.S. PATENT DOCUMENTS

| 2,685,020 A | 7/1954 | Laibow |
| 4,731,522 A | 3/1988 | Manchester |

(Continued)

FOREIGN PATENT DOCUMENTS

| CN | 103930718 B | 8/2017 |
| EP | 1883479 A2 | 2/2008 |

(Continued)

OTHER PUBLICATIONS

PCT/US2015/026353 International Search Report and Written Opinion dated Oct. 14, 2015.

(Continued)

*Primary Examiner* — Michael A Laflame, Jr.
(74) *Attorney, Agent, or Firm* — Quarles & Brady LLP

(57) ABSTRACT

A wax warmer includes a body, an electrical assembly, a base plate, and a sleeve. The electrical assembly is positioned within an interior space of the body and includes an electrical cord that extends outside the body. The sleeve forms an electrical barrier positioned within the interior space and surrounding the electrical assembly. The sleeve is coupled to the base plate and a portion of the electrical cord that passes through an opening in the sleeve is retained by the base plate and the sleeve.

16 Claims, 18 Drawing Sheets

Related U.S. Application Data which is a continuation of application No. 14/255,826, filed on Apr. 17, 2014, now Pat. No. 9,655,168.

(51) Int. Cl.
*H05B 1/02* (2006.01)
*H05B 3/26* (2006.01)

(56) References Cited

U.S. PATENT DOCUMENTS

| | | |
|---|---|---|
| 4,853,517 A | 8/1989 | Bowen et al. |
| 5,647,052 A | 7/1997 | Patel et al. |
| 5,922,231 A | 7/1999 | Karst et al. |
| 6,053,649 A | 4/2000 | Ronai |
| 6,413,476 B1 | 7/2002 | Barnhart |
| 6,627,857 B1 * | 9/2003 | Tanner ............... A61L 9/03 219/445.1 |
| 6,627,858 B2 | 9/2003 | Nomura et al. |
| 6,663,838 B1 | 12/2003 | Soller |
| D485,341 S | 1/2004 | Wu |
| D492,020 S | 6/2004 | Sevy et al. |
| 6,756,567 B1 | 6/2004 | Suen |
| 6,935,535 B2 | 8/2005 | Pandolfi et al. |
| 7,046,919 B2 | 5/2006 | Shimizu et al. |
| 7,059,795 B2 | 6/2006 | Guillaume et al. |
| 7,132,084 B1 | 11/2006 | Roumpos |
| 7,133,605 B2 | 11/2006 | Niemeyer |
| 7,252,805 B2 | 8/2007 | Hart et al. |
| 7,284,741 B2 | 10/2007 | Pierce |
| 7,329,839 B2 | 2/2008 | Palmer |
| 7,377,772 B2 | 5/2008 | Thune et al. |
| D579,645 S | 11/2008 | Guers-Neyraud |
| D585,537 S | 1/2009 | Weggelaar |
| D589,801 S | 4/2009 | Lablaine |
| 7,572,412 B2 * | 8/2009 | Yang ............... A61L 9/122 392/386 |
| D603,034 S | 10/2009 | Thompson |
| D604,627 S | 11/2009 | LaBlaine |
| 7,757,899 B2 | 7/2010 | van der Heijden |
| 7,824,627 B2 | 11/2010 | Michaels et al. |
| 8,020,732 B2 | 9/2011 | van der Heijden |
| 8,042,710 B2 | 10/2011 | van der Heijden |
| 8,056,769 B2 | 11/2011 | van der Heijden |
| 8,066,420 B2 | 11/2011 | Hsiao |
| 8,201,957 B2 | 6/2012 | Hsiao |
| D665,066 S | 8/2012 | Browder |
| 8,262,277 B2 | 9/2012 | Hsiao |
| 8,265,465 B2 | 9/2012 | Jorgensen |
| 8,292,127 B2 | 10/2012 | van der Heijden |
| 8,336,737 B2 | 12/2012 | van der Heijden |
| 8,356,732 B2 | 1/2013 | van der Heijden et al. |
| 8,360,282 B2 | 1/2013 | van der Heijden |
| 8,364,028 B1 | 1/2013 | Pesu et al. |
| D675,528 S | 2/2013 | Beaver |
| 8,412,029 B2 | 4/2013 | Browder et al. |
| 8,430,274 B2 | 4/2013 | van der Heijden et al. |
| 8,567,644 B2 | 10/2013 | Martinez de San Vicente Oliveras |
| 8,668,885 B2 | 3/2014 | Wirz |
| 8,716,632 B1 | 5/2014 | Pesu et al. |
| 8,724,975 B2 | 5/2014 | Browder et al. |
| 8,765,073 B1 | 7/2014 | Hsiao |
| 8,772,675 B2 | 7/2014 | Juarez |
| 8,870,029 B2 | 10/2014 | Stanojlovic et al. |
| 8,873,941 B2 | 10/2014 | Row |
| 8,878,102 B2 | 11/2014 | Juarez |
| 8,938,159 B2 | 1/2015 | Hsiao |
| 8,974,107 B2 | 3/2015 | Hsiao |
| 9,028,759 B2 | 5/2015 | Wirz |
| 9,109,780 B2 | 8/2015 | Hsiao |
| 9,125,956 B2 | 9/2015 | Juarez |
| 9,206,963 B2 | 12/2015 | Hsiao |
| 9,211,355 B2 | 12/2015 | Thompson et al. |
| 9,345,800 B2 | 5/2016 | Juarez |
| 9,370,593 B2 | 6/2016 | Newman |
| 9,399,079 B2 | 7/2016 | McMinn et al. |
| 9,410,695 B2 | 8/2016 | Hsiao |
| 9,498,553 B2 | 11/2016 | Hsiao et al. |
| 9,500,358 B2 | 11/2016 | Hsiao |
| 9,541,279 B2 | 1/2017 | Sharma et al. |
| 9,775,925 B2 | 10/2017 | Juarez |
| 9,775,926 B2 | 10/2017 | Juarez |
| 9,844,609 B2 | 12/2017 | Hsiao |
| 2001/0041317 A1 | 11/2001 | Frandsen |
| 2005/0016985 A1 | 1/2005 | Haas et al. |
| 2005/0074358 A1 | 4/2005 | Hart |
| 2005/0106077 A1 | 5/2005 | Hurwitz |
| 2005/0155985 A1 | 7/2005 | Meyer |
| 2006/0163241 A1 | 7/2006 | Xiao |
| 2006/0175425 A1 | 8/2006 | McGee |
| 2006/0193611 A1 | 8/2006 | Ruiz Ballesteros |
| 2006/0219694 A1 | 10/2006 | Wu |
| 2007/0031298 A1 | 2/2007 | Roumpos et al. |
| 2008/0169311 A1 | 7/2008 | Van Der Heijden |
| 2008/0277426 A1 | 11/2008 | van der Heijden |
| 2008/0314931 A1 | 12/2008 | van der Heijden |
| 2009/0001100 A1 | 1/2009 | van der Heijden |
| 2009/0004614 A1 | 1/2009 | Furner |
| 2009/0020552 A1 | 1/2009 | van der Heijden |
| 2009/0236371 A1 | 9/2009 | van der Heijden |
| 2010/0001024 A1 | 1/2010 | van der Heijden |
| 2010/0096376 A1 | 4/2010 | Hsiao |
| 2010/0133300 A1 | 6/2010 | van der Heijden et al. |
| 2010/0270943 A1 | 10/2010 | Cook |
| 2010/0320232 A1 | 12/2010 | van der Heijden et al. |
| 2011/0110072 A1 | 5/2011 | Hsiao |
| 2011/0110092 A1 * | 5/2011 | Hsiao ............... A61L 9/03 362/253 |
| 2011/0110118 A1 | 5/2011 | Hsiao |
| 2012/0024837 A1 * | 2/2012 | Thompson ............... A61L 9/03 219/433 |
| 2012/0070132 A1 | 3/2012 | Napier |
| 2012/0183280 A1 | 7/2012 | Kowalec et al. |
| 2012/0318779 A1 * | 12/2012 | Juarez ............... H01R 33/22 219/209 |
| 2012/0318780 A1 * | 12/2012 | Juarez ............... H05B 3/26 219/209 |
| 2013/0020307 A1 | 1/2013 | Ashton et al. |
| 2013/0170184 A1 | 7/2013 | Browder et al. |
| 2013/0266297 A1 | 10/2013 | Ihle et al. |
| 2014/0014641 A1 | 1/2014 | Propes |
| 2014/0014736 A1 | 1/2014 | Wirz |
| 2014/0110389 A1 | 4/2014 | Hsiao |
| 2014/0118993 A1 | 5/2014 | Chen |
| 2014/0126891 A1 * | 5/2014 | Hsiao ............... F24F 3/056 392/393 |
| 2014/0133132 A1 | 5/2014 | Hsiao |
| 2014/0158790 A1 | 6/2014 | Gordon et al. |
| 2014/0217624 A1 | 8/2014 | Tepas et al. |
| 2014/0334801 A1 | 11/2014 | Browder et al. |
| 2015/0010293 A1 | 1/2015 | Newman |
| 2015/0108241 A1 | 4/2015 | Chase et al. |
| 2015/0108243 A1 | 4/2015 | Bourne |
| 2015/0174278 A1 | 6/2015 | Belongia |
| 2015/0231296 A1 | 8/2015 | Juarez |
| 2015/0283280 A1 | 10/2015 | Belongia |
| 2015/0305089 A1 | 10/2015 | Belongia et al. |
| 2015/0320898 A1 | 11/2015 | Juarez |
| 2015/0352563 A1 | 12/2015 | Borra et al. |
| 2016/0089466 A1 | 3/2016 | McMinn et al. |
| 2016/0195257 A1 | 7/2016 | Hsiao |
| 2016/0375168 A1 | 12/2016 | Hsiao |
| 2016/0375169 A1 | 12/2016 | Hsiao |
| 2017/0232126 A1 | 8/2017 | Faterioun et al. |

FOREIGN PATENT DOCUMENTS

| | | |
|---|---|---|
| EP | 1976642 A2 | 10/2008 |
| EP | 2040851 B1 | 10/2010 |
| EP | 2094394 B1 | 11/2010 |
| EP | 1976643 B1 | 8/2011 |
| EP | 1976644 B1 | 6/2012 |
| EP | 1981646 B1 | 4/2013 |

(56) References Cited

FOREIGN PATENT DOCUMENTS

| | | |
|---|---|---|
| EP | 2139607 B1 | 2/2014 |
| EP | 2694219 A1 | 2/2014 |
| EP | 2200750 B1 | 2/2015 |
| TW | I589311 B | 7/2017 |
| WO | 2006118445 A2 | 11/2006 |
| WO | 2007064277 A1 | 6/2007 |
| WO | 2007086730 A2 | 8/2007 |
| WO | 2007086731 A1 | 8/2007 |
| WO | 2007086732 A1 | 8/2007 |
| WO | 2007091882 A1 | 8/2007 |
| WO | 2008007943 A1 | 1/2008 |
| WO | 2008072949 A2 | 6/2008 |
| WO | 2008133491 A1 | 11/2008 |
| WO | 2009038452 A1 | 3/2009 |
| WO | 2009038454 A2 | 3/2009 |
| WO | 2009136781 A1 | 11/2009 |
| WO | 2011072209 A1 | 6/2011 |
| WO | 2012099654 A1 | 7/2012 |
| WO | 2012138220 A1 | 10/2012 |
| WO | 2012173861 A2 | 12/2012 |
| WO | 2014102257 A1 | 7/2014 |
| WO | 2015161185 A2 | 10/2015 |
| WO | 2016025706 A1 | 2/2016 |
| WO | 2016146671 A1 | 9/2016 |
| WO | 2018029043 A1 | 2/2018 |

OTHER PUBLICATIONS

International Search Report and Written Opinion issued in corresponding International Application No. PCT/US2018/055415, dated Jan. 18, 2019, 8 pages.

* cited by examiner

ELECTRICAL BARRIER FOR WAX WARMER

CROSS REFERENCE TO RELATED APPLICATIONS

This application claims priority to and is a continuation-in-part of U.S. patent application Ser. No. 15/595,645, which was filed on May 15, 2017, which is a continuation of U.S. patent application Ser. No. 14/255,826, which was filed on Apr. 17, 2014 and issued as U.S. Pat. No. 9,655,168.

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Invention

The present disclosure generally relates to an electrical barrier for a wax warmer, and more specifically, to an electrical barrier that inhibits a user from contacting live electrical components when a body of the wax warmer is broken or damaged.

2. Description of the Background of the Invention

Candles have been used for centuries to provide illumination and pleasant aromas to the surrounding environment. At its most basic level, a candle consists of a wick dipped in wax. The wick is lit and provides light while the burning or melting wax may provide a pleasant aroma. Alternatively, unscented or scented candles or wax melts can be placed in a warmer. These candles or warmers may also be used to provide more than just illumination and/or pleasant fragrances. For instance, candles and warmers may be placed outside around a patio or deck. The wax or oil may include materials with insect repellant properties along with providing a pleasant aroma and/or illumination. Generally, users can burn or warm waxes and oils to provide desired effects to the surrounding atmosphere or environment.

Traditional warmers and candles that utilize a live flame may have some drawbacks. Candles may be forgotten and left unsupervised and may represent a fire hazard. Also, a candle flame may be extinguished with a slight breeze or gust of wind. An additional drawback associated with candles is the inability to control the intensity of the heat being provided to the scented material. A candle flame is not easily adjustable and thus the amount of heat the flame provides to the infused wax or oil does not allow a user to vary the strength of the fragrance introduced into the surrounding environment.

Some attempts have been made to overcome the aforementioned drawbacks associated with live flame warmers and candles through the use of electric wax warmers. An electric wax warmer consists of a heater in thermal contact with a reservoir for holding a wax melt or infused oil. The heater replaces the candle in a traditional warmer and melts the wax or heats the oil in the reservoir, resulting in the same benefits as previously mentioned. The lack of a flame reduces the risks associated with traditional warmers and candles. Another advantage may be the temperature of the heater in an electric wax warmer can be adjusted. This provides the user with more control over the amount of fragrant or other materials introduced into the surrounding environment. Electric wax warmers also have more consistent performance indoors and outdoors and are less messy than traditional candles and warmers.

Electric wax warmers may have significant advantages over traditional warmers and candles, however, they may also have some drawbacks. Many of the traditional electric wax warmers include a housing, commonly constructed of a ceramic material, which encloses the various electrical components necessary for heating the wax melt or infused oil. Thus, if the ceramic housing is broken, the various electrical components may be exposed, allowing a user to come into contact with live electrical components.

Attempts have been made by some standards setting organizations to require such ceramic housings to pass a ball impact test. For example, the UL 283 standard for air fresheners and deodorizers requires ceramic wax warmers to undergo an impact performance test using a 535 gram, 5.08 centimeter diameter smooth, solid steel ball that is dropped from a specified height of 60 centimeters. Once the steel ball is dropped onto the ceramic housing, a finger probe may be used, assuming the ceramic housing is damaged, in an attempt to contact the electrical components of the wax warmer. According to the UL 283 standard, if the finger probe can contact the electrical components through the broken ceramic housing, the wax warmer does not pass the ball impact test.

Interestingly, traditional wax warmers often do not pass the ball impact test required by the UL 283 standard. Further, other wax warmers must use stronger or alternative materials to resist cracking, which increases the cost of manufacturing. Therefore, there is a need for an electric wax warmer that overcomes the aforementioned drawbacks.

The present disclosure overcomes some of the aforementioned drawbacks by providing an electrical barrier for a wax warmer that is in compliance with the UL 283 standard. Thus, the present disclosure satisfies the existing need for a wax warmer that includes an electrical barrier to inhibit a user from contacting live electrical components. Further still, the present disclosure satisfies the need for an electrical barrier for a wax warmer that is easy to manufacture, thus keeping manufacturing costs and material usage down.

SUMMARY OF THE INVENTION

According to one aspect, a wax warmer includes a body, an electrical assembly, a base plate, and a sleeve. The electrical assembly is positioned within an interior space of the body and includes an electrical cord that extends outside the body. The sleeve forms an electrical barrier positioned within the interior space and surrounding the electrical assembly. The sleeve is coupled to the base plate and a portion of the electrical cord that passes through an opening in the sleeve is retained by the base plate and the sleeve.

According to another aspect, a wax warmer includes a body, an electrical assembly, an electrical cord, and an annular sleeve. The electrical assembly is positioned within an interior space of the body. The electrical cord couples to the electrical assembly. The annular sleeve is positioned within the interior space of the body. The annular sleeve surrounds the entire electrical assembly and retains a portion of the electrical cord within the body.

According to a further aspect, a wax warmer includes a body, a reservoir, an electrical assembly, and an annular sleeve. The body includes a top plate and a base plate. The reservoir is positioned on the top plate of the body. The electrical assembly is positioned within an interior space of the body. The annular sleeve is coupled to the base plate and forms an electrical barrier. The annular sleeve is also positioned within the interior space and surrounds the electrical assembly within the body.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
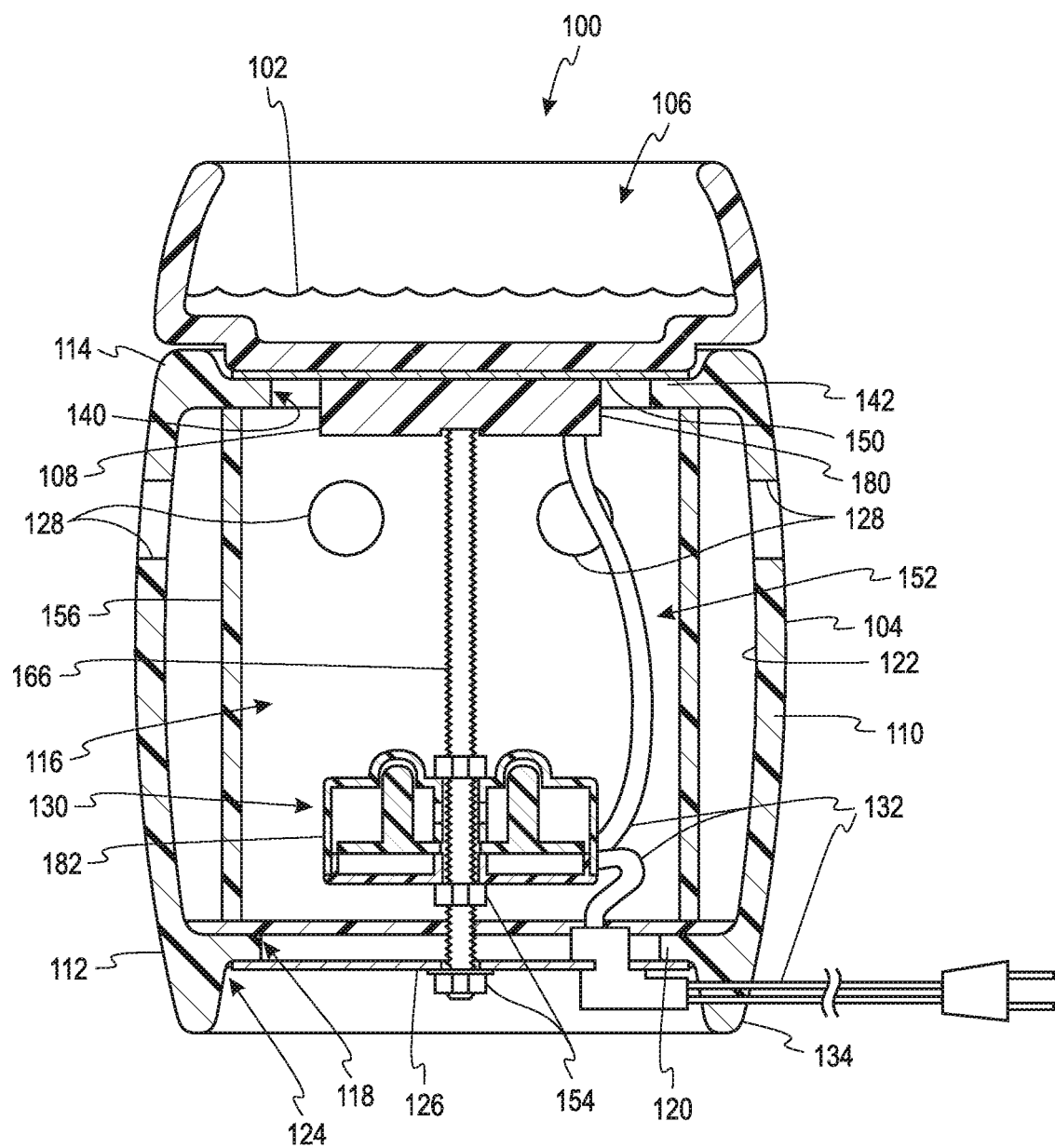
FIG. 1 is a cross-sectional side elevational view of a wax warmer.

Referring to FIG. 1, a wax warmer 100 is depicted. The wax warmer 100 is designed to heat a wax melt 102 and thereby release a fragrance or other material contained therein into the surrounding environment. The wax warmer 100 generally includes a body 104, a reservoir 106, and a heater assembly 108. The body 104 is fashioned to house the heater assembly 108 and provide a support structure for the reservoir 106. The wax warmer 100 is generally described to include the aforementioned components, but the wax warmer 100 may be adapted to add or remove various components according to specific user requirements.

Still referring to FIG. 1, the body 104 includes a sidewall 110 having a bottom end 112 and a top end 114. In the present embodiment, the sidewall 110 is generally cylindrical in shape and defines an interior space 116. The bottom end 112 defines a first opening 118. A lip 120 extends from an inner surface 122 of the sidewall 110. The bottom end 112 and the lip 120 form a recess 124 adapted to receive a base plate 126 that is disposed adjacent the bottom end 112 of the body 104. Portions of the bottom end 112 of the body 104 may include extensions (not shown) or other structures (feet, pads, structures with high coefficients of friction, etc.) generally known to those having ordinary skill in the art to provide stability to the wax warmer 100.

The sidewall 110 further includes one or more apertures 128 provided therein. The apertures 128 may be adapted to receive a light emissive or transmissive cover (not shown) and/or an indicator, such as an LED, or sensor (not shown). For example, the apertures 128 may allow light, provided by an electrical light source 130, from the interior space 116 to be visible through the apertures 128. Additionally, one or more of the apertures 128 may be fully or partially unobstructed to facilitate cooling of the body 104 and/or the flow of air through the interior space 116 of the wax warmer 100. The apertures 128 may be any desired shape and size for aesthetics, cooling, and light passage. For example, and without limitation, the apertures 128 may be circular (as shown in FIG. 1), triangular, rectangular, polygonal, star-shaped, crescent-shaped, irregularly-shaped, flower-shaped, etc. A second aperture 134 is also provided proximal to the bottom end 112 of the sidewall 110. Preferably, the second aperture 134 provides a pass-through for an electrical cord 132 in electrical communication with the electrical light source 130 and the heater assembly 108.

Referring still to FIG. 1, a second opening 140 is provided at the top end 114 of the sidewall 110. The second opening 140 is bounded by a shoulder 142 extending radially inwardly from the inner surface 122 of the sidewall 110. The second opening 140 and the shoulder 142 are adapted to receive the heater assembly 108 and the reservoir 106.

It has been contemplated that the body 104 and the reservoir 106 are preferably made from a ceramic material. However, any other materials as known to those having ordinary skill in the art may be used, such as plastic, metal, stone or other natural materials, etc. The body 104 and the reservoir 106 may take any geometric shape, e.g. a square, to provide different appearances. Further, the exterior surfaces of the body 104 and the reservoir 106 may be provided with any type of surface indicia, raised patterns, or any other decorations to configure the wax warmer 100 for aesthetic purposes.

With continued reference to FIG. 1, an electrical assembly 152 of the wax warmer 100 described above may be at least partially disposed within the interior space 116 of the body 104. The electrical assembly 152 may include the heater assembly 108 and the electrical light source 130. In some embodiments, structural components may hold some of the various components in place. For example, a threaded rod 166 may extend through the base plate 126 and the electrical light source 130 and may abut against the heater assembly 108. At least one nut 154 may hold the threaded rod 166 and the various components in place.

The heater assembly 108 may be positioned within the body 104 proximate the second opening 140 such that the heater assembly 108 may heat the wax melt 102 in the reservoir 106. In some embodiments, the electrical light source 130 may be positioned within the body 104 at a location distant to that of the heater assembly 108, such as proximate the first opening 118 of the bottom end 112. In other embodiments, the electrical light source 130 may be positioned within the body 104 at a location proximate the heater assembly 108. The heater assembly 108 may be a heat source such as a resistance heater, an incandescent light bulb, a PTC heater, or any other heater known to one in the art.

In one preferred embodiment, the wax warmer 100 includes a top plate 150 under the reservoir 106. The top plate 150 may be formed from a metallic material and disposed adjacent the top end 114 of the body 104. The heater assembly 108 may be abutted against or otherwise thermally coupled to a surface of the top plate 150. By way of non-limiting examples, the heater assembly 108 may be coupled to the top plate 150 with an adhesive, with a mechanical connection (e.g., a clip, screw, interference fit, etc.), by being pushed against the top plate 150 with the threaded rod 166 (as shown), or any combination thereof. In embodiments in which the reservoir 106 and the body 104 are separate and detachable, the top plate 150 may be attached to one of the reservoir 106 or the body 104 or neither. In some embodiments, the wax warmer 100 may not include the top plate 150. In such embodiments, the heater assembly 108 may abut directly against a bottom of the reservoir 106.

Figure 2:
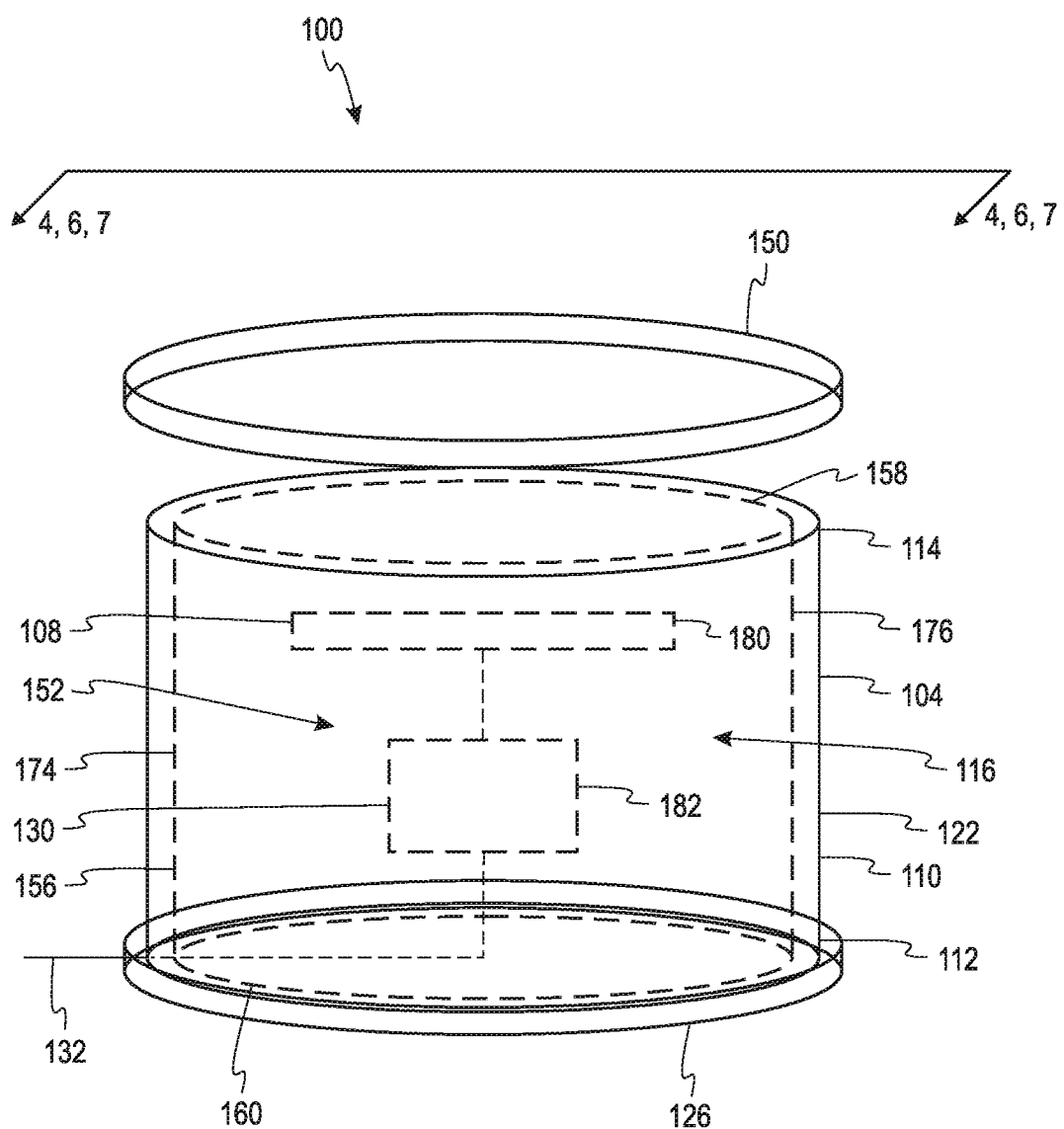
FIG. 2 is a schematic view of a wax warmer with an electrical barrier.

Turning now to FIG. 2, a simplified schematic diagram of the wax warmer 100 is shown. The wax warmer 100 includes substantially the same components as described with reference to FIG. 1, therefore similar reference numerals will be used.

Figure 9:
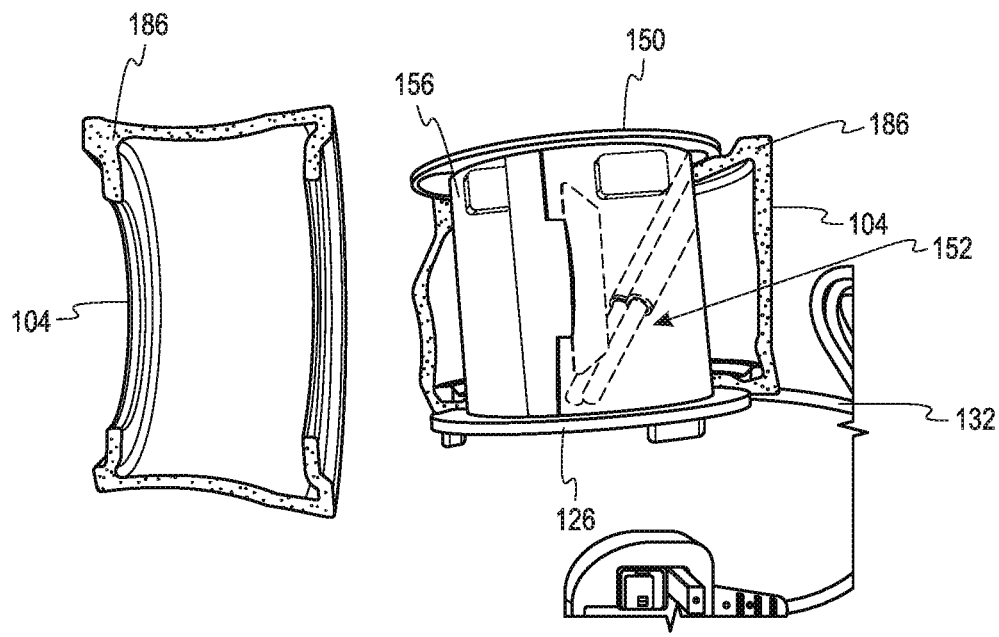
FIG. 9 is an image of the wax warmer of FIG. 8 after the ball impact test showing an electrical barrier.

An electrical barrier 156 is positioned inside the body 104 of the wax warmer 100 in the embodiment shown in FIG. 2 (see also FIG. 1). The electrical barrier 156 may take the form of an annular sleeve, for example, and surround the electrical assembly 152. Thus, if the body 104 of the wax warmer 100 is damaged or broken, as shown in FIG. 9, the electrical assembly 152, including the heater assembly 108 and electrical light source 130, are not exposed to a user of the wax warmer 100. In addition, the electrical barrier 156 ensures that the wax warmer 100 is in compliance with standards related to air fresheners and deodorizers, such as the UL 283 standard, as will be described in further detail below.

Figure 3A:
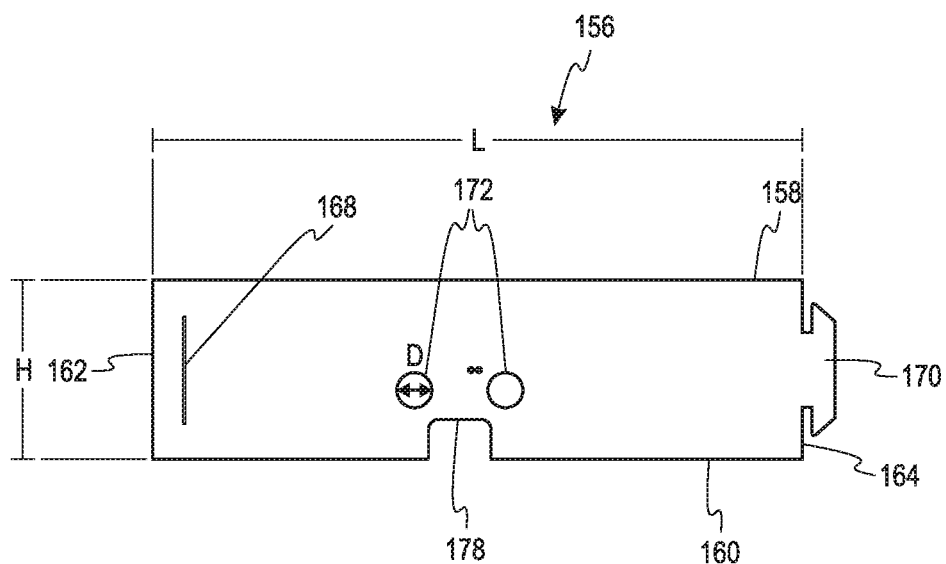
FIG. 3A is a side elevational view of an electrical barrier layout according to one embodiment of the disclosure.
Figure 3B:
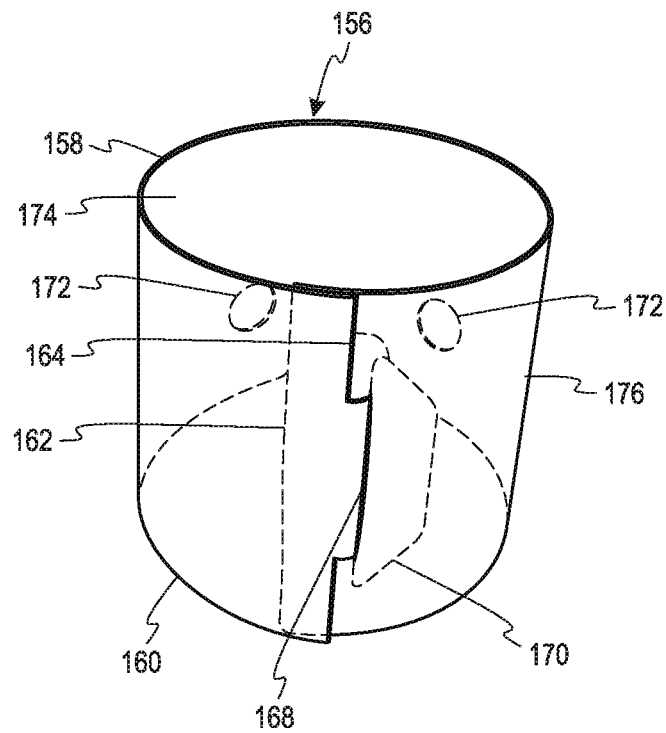
FIG. 3B is a perspective view of the electrical barrier of FIG. 3A coupled together to form a generally cylindrical shape.

A first embodiment of the electrical barrier 156 is shown in FIGS. 3A and 3B. The electrical barrier 156 can begin as a flat, substantially rectangular layout, as shown in FIG. 3A having a length dimension L and a height dimension H. The length dimension L and the height dimension H may vary depending on the dimensions of the particular wax warmer 100 the electrical barrier 156 is used in. In a preferred embodiment, the length dimension L is about 22.5 centimeters, and the height dimension H is about 5.7 centimeters. The electrical barrier 156 may have a thickness dimension T (see FIG. 4) that is preferably between about 0.025 centimeters and about 0.15 centimeters. However, the length dimension L may be any suitable length to allow the electrical barrier 156 to fit within the body 104 of the wax warmer 100. Similarly, the height dimension H may be of any height to allow the electrical barrier 156 to fit within the body 104 and not extend beyond the base plate 126 or the top plate 150 of the wax warmer 100. Likewise, the thickness dimension T may vary depending on the specific wax warmer 100 that the electrical barrier 156 is used in. For example, depending on the heater assembly 108 used in a particular wax warmer 100, the thickness dimension T may change in order to withstand a variety of heat outputs.

Turning again to FIG. 3A, the electrical barrier 156 includes a top edge 158 and a bottom edge 160 that extend the length dimension L. In the present embodiment, the top edge 158 is parallel to the bottom edge 160. A first side edge 162 and a second side edge 164 extend about the height dimension H. In the present embodiment, the first and second side edges 162, 164 are substantially parallel to one another. A groove 168 is provided adjacent to the first side edge 162, and a tongue portion 170 is provided adjacent to the second side edge 164. As shown in FIG. 3B, the groove 168 is configured to receive the tongue portion 170 to form a substantially cylindrical electrical barrier 156. Alternatively, the first side edge 162 and the second side edge 164 may be heat sealed, adhered, or coupled together using any suitable mechanical fastener (e.g., a staple or a rivet). In yet another alternative embodiment, the first side edge 162 and the second side edge 164 may be integrally molded together to form the electrical barrier 156.

Figure 4:
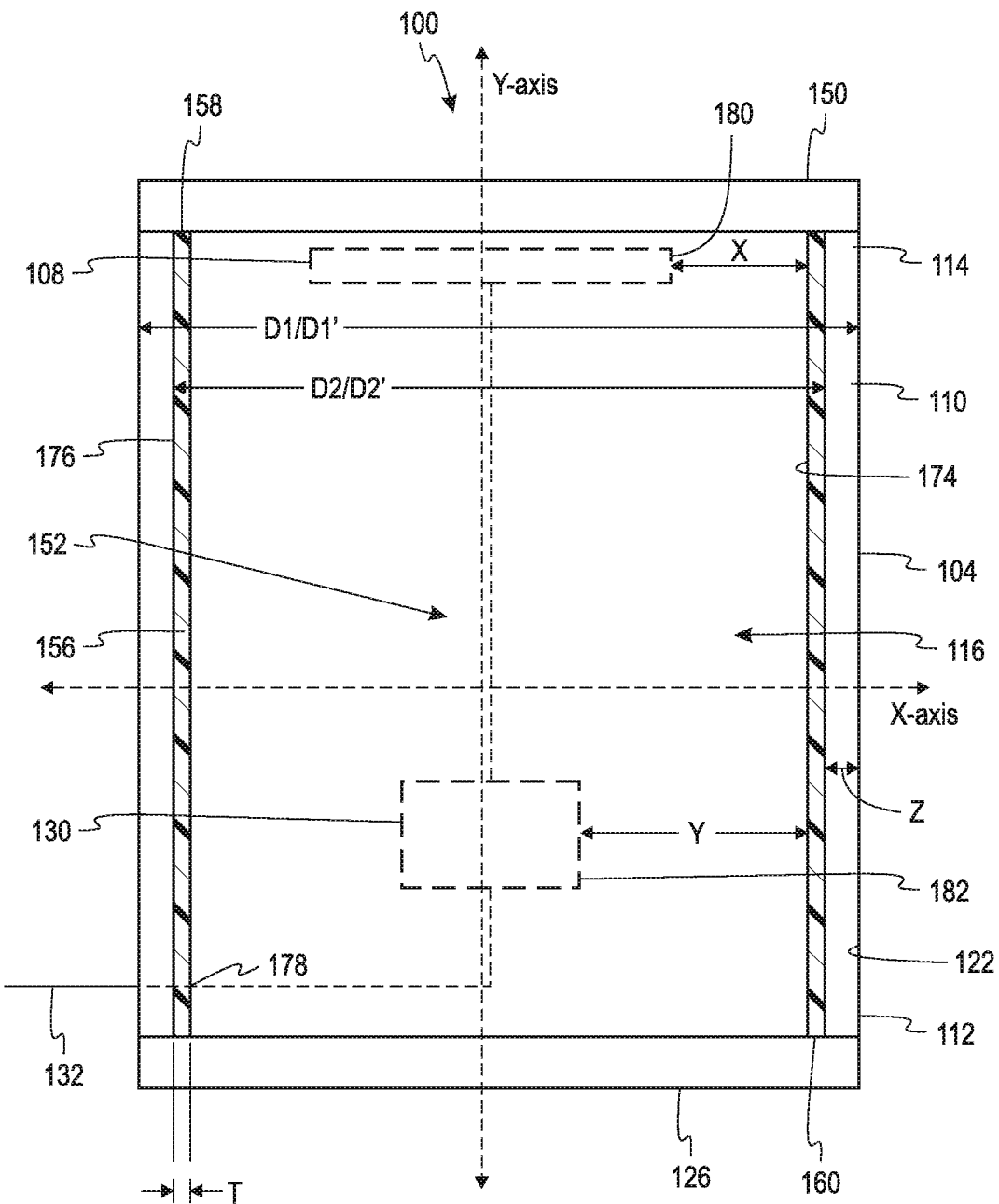
FIG. 4 is a cross-sectional view of the wax warmer taken generally along the line 4-4 of FIG. 2 with the electrical barrier in a first position.

In some embodiments, the electrical barrier 156 may take the form of a sleeve that has a substantially circular cross-section when taken through a horizontal axis (axis-x in FIG. 4). In other embodiments, the horizontal cross-section of the electrical barrier 156 is oval, circular, curvilinear, triangular, or any suitable shape in order to shield the electrical assembly 152. In the embodiment shown in FIGS. 3A and 3B the electrical barrier 156 is a right circular cylinder. However, the electrical barrier 156 can also take the form of an elliptic cylinder, an oblique cylinder, a parabolic cylinder, a hyperbolic cylinder, etc.

Still referring to FIGS. 3A and 3B, the electrical barrier 156 may include one or more apertures 172 that extend from an interior surface 174 to an exterior surface 176 of the electrical barrier 156. The one or more apertures 172 may include a diameter D that is not to exceed 0.95 centimeters. In other embodiments, the diameter D of the one or more apertures 172 is between about 0.64 centimeters and about 0.95 centimeters. A maximum diameter D is established such that in the event the body 104 of the wax warmer 100 is broken or damaged, a user is inhibited from contacting any of the components of the electrical assembly 152. Or, alternatively, during a standardized ball impact test, a finger probe (not shown) is inhibited from contacting any of the components of the electrical assembly 152 to maintain compliance with the UL 283 standard, for example.

The purpose of the one or more apertures 172 disposed on the surfaces 174, 176 of the electrical barrier 156 is to allow light, provided by the electrical light source 130, to be visible through the apertures 128 on the body 104. Additionally, the apertures 172 may facilitate cooling of the body 104 as heated air builds up within the interior space 116 during use of the wax warmer 100. The apertures 172 may be any desired shape for aesthetics, cooling, and light passage. The electrical barrier 156 may further include a slot 178, as shown in FIG. 3A, disposed along the bottom edge 160 of the electrical barrier 156. The slot 178 may be substantially sized so as to provide a passage for the electrical cord 132 to pass through the electrical barrier 156 and through the second aperture 134 (see FIG. 1) of the body 104.

Figure 5A:
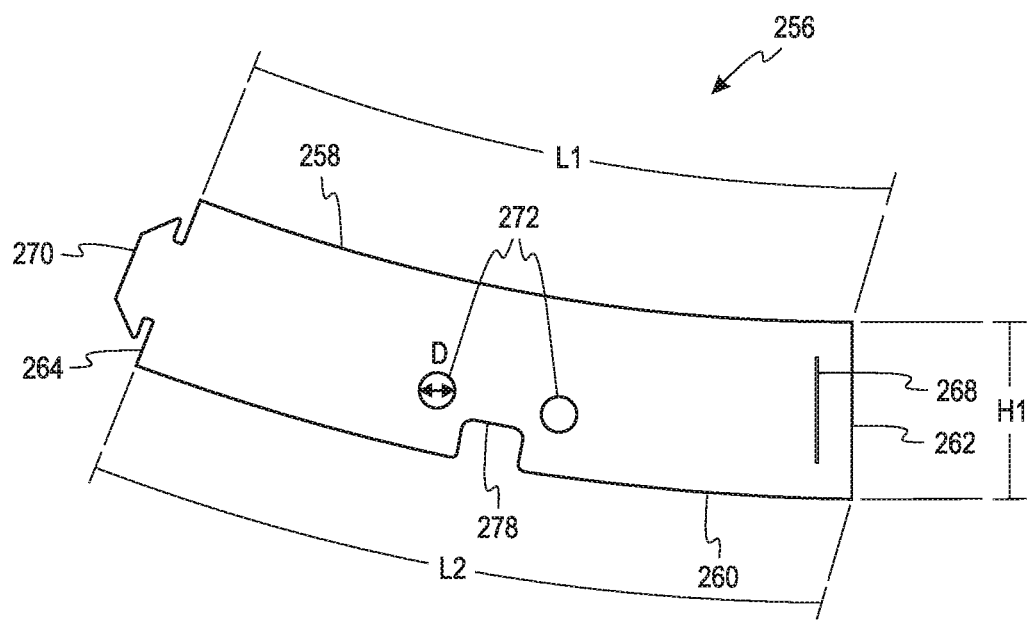
FIG. 5A is a side elevational view of an electrical barrier layout according to another embodiment of the disclosure.
Figure 5B:
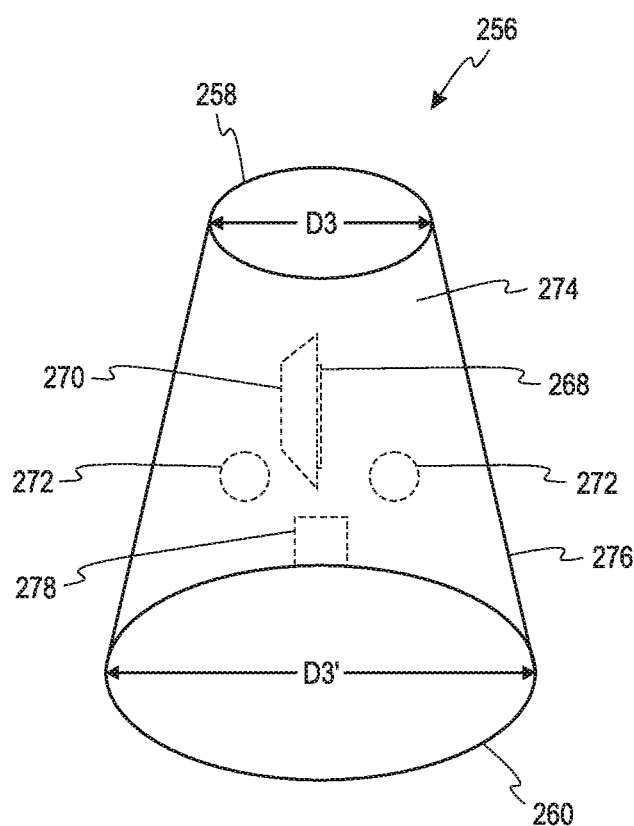
FIG. 5B is a perspective view of the electrical barrier of FIG. 5A coupled together to form a generally frusto-conical shape.

In an alternative embodiment, as shown in FIGS. 5A and 5B, a non-cylindrical electrical barrier 256 is provided that is substantially frusto-concial shaped. Similar to the cylindrical shaped electrical barrier 156, the frusto-conical shaped electrical barrier 256 can begin as a flat layout, as shown in FIG. 5A. Because the electrical barrier 256 is frusto-conical shaped, the top edge 258 may be slightly curved and have a length dimension L1, and the bottom edge 160 may also be slightly curved and have a length dimension L2. The length dimension L1 is measured as a curved line from the first side edge 262 to the second side edge 264 along the top edge 258. Similarly, the length dimension L2 is measured as a curved line from the first side edge 262 to the second side edge 264 along the bottom edge 260. Thus, the length dimension L1 is less than the length dimension L2. In a preferred embodiment, the length dimension L1 is about 20.9 centimeters, and the length dimension L2 is about 22.5 centimeters. The electrical barrier 256 also includes a height dimension H1 along the first side edge 262 and the second side edge 264 that is about 5.7 centimeters. The height dimension H1 is measured from the top edge 258 to the bottom edge 260 along either of the side edges 262, 264. The length dimensions L1 and L2 and the height dimension H1 may vary depending on the dimensions of the particular wax warmer 100 the electrical barrier 256 is used in. Thus, the length dimensions L1 and L2 may be any suitable length to allow the electrical barrier 256 to fit within the body 104 of the wax warmer 100. Similarly, the height dimension H1 may be of any height to allow the electrical barrier 256 to fit within the body 104 and not extend beyond the base plate 126 or the top plate 150. The electrical barrier 256 may have a thickness dimension (not shown) that is substantially the same as the thickness dimension T (see FIG. 4) of the cylindrical electrical barrier 156.

Due to the varying length dimensions L1 and L2, the frusto-conical shaped electrical barrier 256 has a minor diameter D3 at the top edge 258 that is less than a major diameter D3' at the bottom edge 260 (see FIG. 5B). In one embodiment, the minor diameter D3 is about 6.4 centimeters, and the major diameter D3' is about 6.7 centimeters. In contrast, the cylindrical shaped electrical barrier 156, as shown in FIG. 4, includes a uniform diameter D2 at the top end 114 and the bottom end 112 of the wax warmer 100 (see FIG. 4). The diameter D2 may be, in one embodiment, at least about 5.7 centimeters. However, the minor and major diameters D3 and D3', and the diameter D2, can vary depending on the aesthetic design, for example, of the wax warmer 100. Thus, the minor and major diameters D3 and D3' and the diameter D2 may be any suitable size to allow the frusto-conical shaped electrical barrier 256 or the cylindrical shaped electrical barrier 156 to fit within the body 104 of the wax warmer 100.

Referring again to FIGS. 5A and 5B, a groove 268 may be provided adjacent to the first side edge 262, and a tongue portion 270 may be provided adjacent to the second side edge 264. As shown in FIG. 5B, the groove 268 is configured to receive the tongue portion 270 to form the substantially frusto-conical shaped electrical barrier 256. Alternatively, the first side edge 262 and the second side edge 264 may be heat sealed, adhered, or coupled together using any suitable mechanical fastener (e.g., a staple or a rivet). In yet another alternative embodiment, the first side edge 262 and the second side edge 264 may be integrally molded together to form the electrical barrier 256.

Still referring to FIGS. 5A and 5B, the electrical barrier 256 may include one or more apertures 272 that extend from an interior surface 274 to an exterior surface 276 of the electrical barrier 256. The one or more apertures 272 may include a diameter D that is not to exceed 0.95 centimeters for the same reasons as previously described. In other embodiments, the diameter D of the one or more apertures 272 is between about 0.64 centimeters and about 0.95 centimeters.

The electrical barriers 156 and 256 of the present embodiments may be constructed of a polymeric material (e.g., polycarbonate, polypropylene, etc.), a mica material, or a horizontal burning (HB) material, for example. In some embodiments, the electrical barriers 156 and 256 may be constructed of any suitable flexible material. However, it is contemplated that a rigid material, such as a mica material, may be used for the electrical barriers 156 and 256.

The material of the electrical barriers 156 and 256 preferably includes a specific melting temperature above the maximum heat output of the heater assembly 108 used within the wax warmer 100. More preferably, the material of the electrical barriers 156 and 256 has a specific melting temperature above the combined heat output of the electrical assembly 152, which may include one or more of a heater(s), a light(s), a sensor(s), or other electrical component(s) capable of outputting heat. Therefore, the electrical barriers 156 and 256 preferably have a melting temperature between about 350 degrees Fahrenheit and about 510 degrees Fahrenheit. For example, in one non-limiting embodiment, the electrical light source 130 may provide a heat output ranging from about 10 watts to about 20 watts. Similarly, the heater assembly 108 may include a resistive heater, which has a heat output ranging from about 10 watts to about 20 watts.

Turning now to FIG. 4, the electrical barrier 156 is shown positioned within the body 104 of the wax warmer 100 and surrounding the electrical assembly 152. In some embodiments, the electrical barrier 156 is positioned a distance X from the electrical assembly. In the present scenario, the distance X may be defined as the distance from the interior surface 174 of the electrical barrier 156 to an exterior surface 180 of the heater assembly 108. The distance X may be measured in a horizontal plane defined by the x-axis shown in FIG. 4. Additionally, or alternatively, the electrical barrier 156 is positioned a distance Y from the electrical light source 130. The distance Y may be defined as the distance from the interior surface 174 of the electrical barrier 156 to an exterior surface 182 of the electrical light source 130. The distance Y may also be measured in a horizontal plane defined by the x-axis shown in FIG. 4. In one embodiment, the distance Y is 0.5 centimeters. In a preferred embodiment, the distance X is a minimum distance of about 0.3 centimeters. In some embodiments, however, minimum distances for X and Y may vary depending on the specific heater assembly 108 or electrical light source 130 used in the wax warmer 100.

The minimum distances X and Y may, in some embodiments, be directly correlated to a ratio of the heat output of the heater assembly 108 or the electrical light source 130 (as measured in watts) to the predetermined melting temperature (as measured in degrees Fahrenheit) of the material of the electrical barrier 156. In a preferred embodiment, the ratio of the heat output to the predetermined melting temperature is between about 0.02 and 0.05. Thus, the higher the heat output produced by either the heater assembly 108 or the electrical light source 130, the greater the distance X and/or Y will be.

In one specific embodiment, the electrical barriers 156 and 256 may be comprised of 100% polymeric materials, which may include one or more materials, and have a thermal rating of at least 230 degrees Fahrenheit and a modulus of elasticity of between 1.5 GPa and 2.6 GPa. Further, in this contemplated embodiment, the electrical barrier 156, 256 has a diameter, or minor diameter, of at least 5.7 centimeters Still referring to FIG. 4, the electrical barrier 156 may be positioned a distance Z from the sidewall 110 of the body 104. The distance Z may be measure from the exterior surface 176 of the electrical barrier 156 to the inner surface 122 of the sidewall 110. In an alternative embodiment, the electrical barrier 156 may be in direct contact with the inner surface 122 of the sidewall 110. However, regardless of the distance Z, the diameter D2 of the electrical barrier 156 is less than a diameter D1 of the body 104 to allow the electrical barrier 156 to be positioned within the body 104. Similarly, with reference to the frusto-conical shaped electrical barrier 256 (see FIGS. 5A and 5B), the diameters D3 and D3' are less than the diameter D1 of the body 104.

Figure 6:
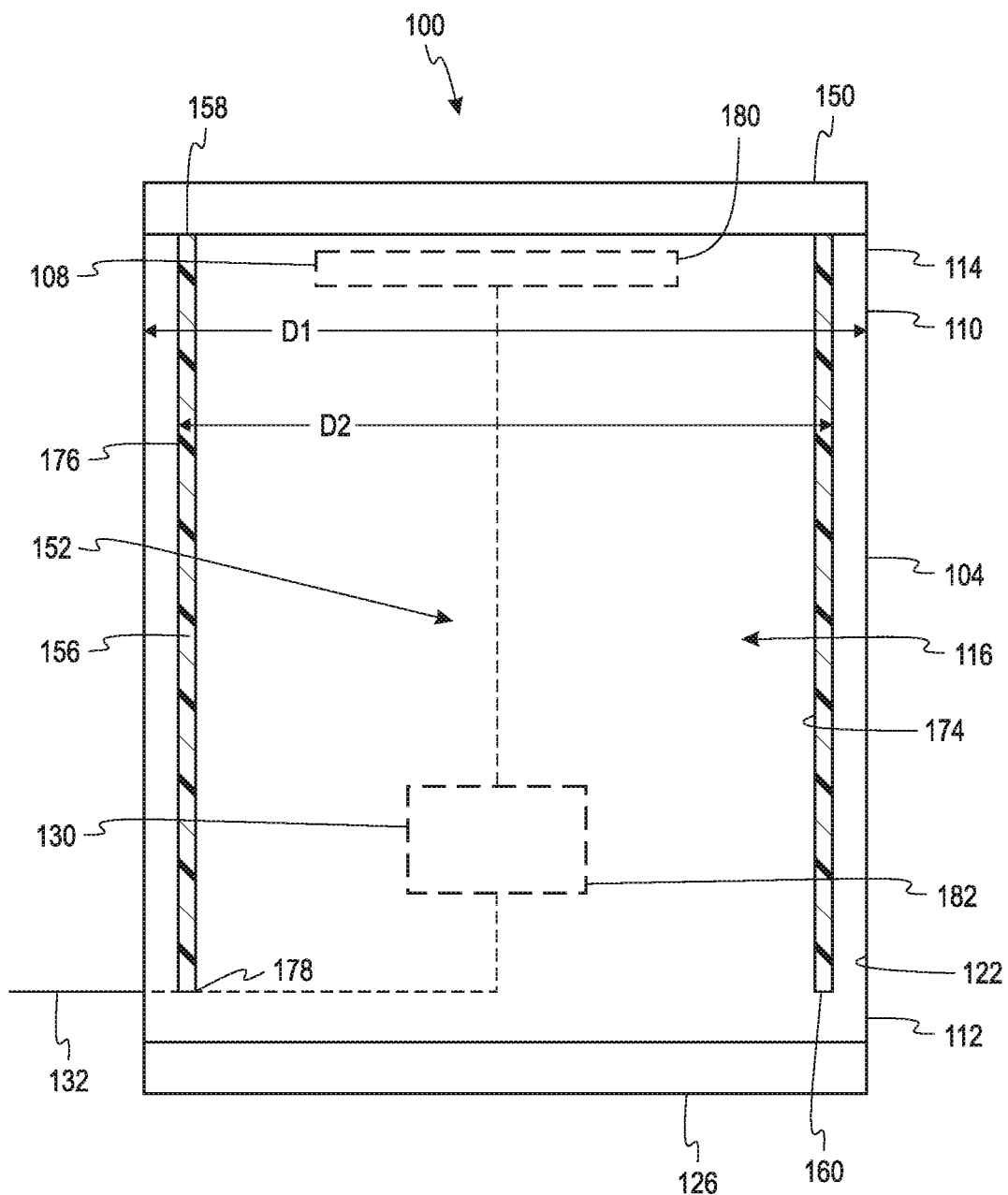
FIG. 6 is a cross-sectional view of the wax warmer taken generally along the line 6-6 of FIG. 2 with the electrical barrier in a second position.
Figure 7:
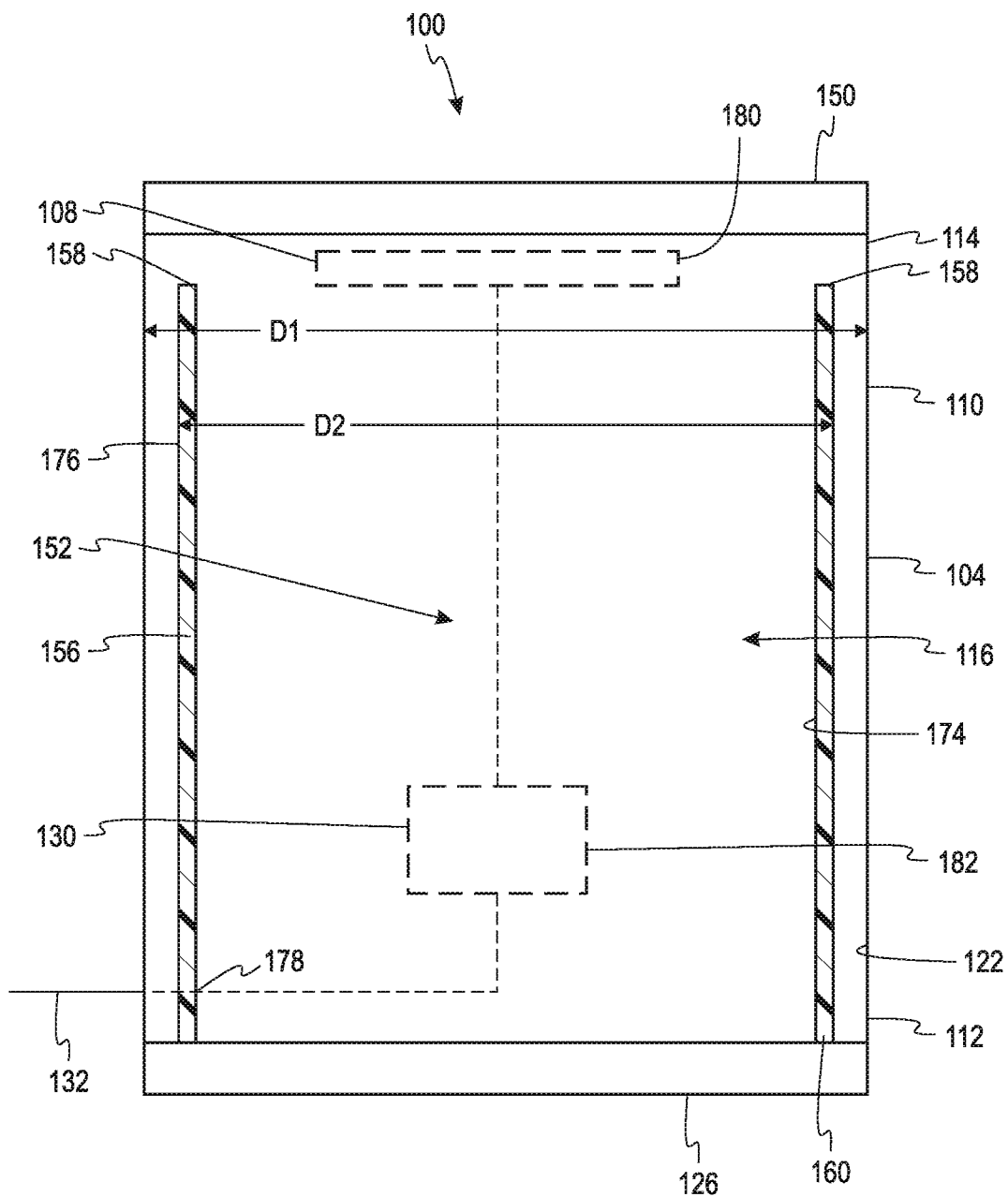
FIG. 7 is a cross-sectional view of the wax warmer taken generally along the line 7-7 of FIG. 2 with the electrical barrier in a third position.

As shown in FIG. 4, the top edge 158 of the electrical barrier 156 is in direct contact with the top plate 150, and the bottom edge 160 is in direct contact with the base plate 126. In an alternative embodiment, as shown in FIG. 6, the top edge 158 of the electrical barrier 156 is in direct contact with the top plate 150, and the bottom edge 160 is not in direct contact with the base plate 126, such that the electrical barrier 156 extends from the top plate 150 toward the bottom end 112 of the body 104. In yet another alternative embodiment, as shown in FIG. 7, the top edge 158 of the electrical barrier 156 is not in direct contact with the top plate 150, and the bottom edge 160 is in direct contact with the base plate 126, such that the electrical barrier 156 extends from the base plate 126 toward the top end 114 of the body 104. When either of the edges 158 and 160 are in direct contact with either of the plates 126 and 150, the connection can be made by a press fit, interference fit, integral molding or extrusion, or any other means providing for a substantially immovable fit as would be known to one of ordinary skill in the art.

Figure 8:
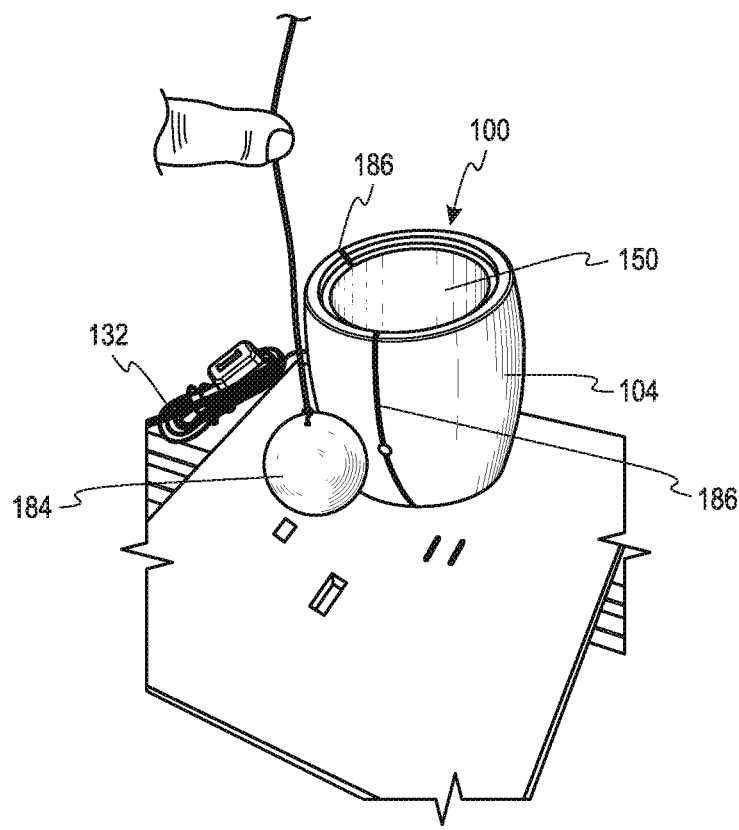
FIG. 8 is an image of a wax warmer undergoing a ball impact test.

Turning now to FIGS. 8 and 9, the embodiments of the wax warmer 100 are shown after a ball impact test is performed as required by the UL 283 standard for air fresheners and deodorizers. First, a steel ball 184 is configured to impact the body 104 of the wax warmer 100 from a specified distance of approximately 60 centimeters. The steel ball 184 may weigh approximately 535 grams and have a diameter of about 5.08 centimeters. As shown in FIG. 8, after the steel ball 184 engages the body 104, cracks 186 may form and the electrical assembly (not shown) is unexposed and inaccessible to a user's finger. As shown in FIG. 9, the body 104 has been removed from the wax warmer 100 after impact of the steel ball 184 and shows the electrical barrier 156 shielding the electrical assembly. Thus, the wax warmer 100 has passed the ball impact test according to the UL 283 standard. More specifically, although cracks 186 are present on the body 104, a finger probe (not shown) is incapable of contacting the electrical assembly 152 of the wax warmer 100 due to the presence of the electrical barrier 156. According to the UL 283 standard, if the finger probe can contact the electrical components through the broken ceramic housing, the wax warmer does not pass the ball impact test.

In contrast, conventional wax warmers typically fail the ball impact test since an electrical barrier is not present. Once the steel ball impacts a conventional wax warmer, the ceramic body breaks and the electrical components are exposed. A user and/or a finger probe can contact the live electrical components, making conventional wax warmers non-compliant with the UL 283 standard.

The wax warmer 100 in the embodiments depicted herein may be assembled quickly and efficiently. A wire harness (not shown) is first connected to the heater assembly 108, the electrical light source 130, and the electrical cord 132. It is contemplated that the electrical cord 132 may be replaced by batteries (not shown) contained within the body 104. It is further contemplated that any suitable electrical power source know to those having ordinary skill in the art may suffice. The next step in assembly is to insert the electrical assembly 152 (i.e., the heater assembly 108 and the electrical light source 130) into the interior space 116 of the body 104. Next, the electrical barrier 156/256 is inserted into the interior space 116 of the body 104 to surround the electrical assembly 152. Lastly, the base plate 126 is attached to the bottom end 112 of the body 104.

FIGS. 10-22 depict an embodiment of a wax warmer 300 and its components. The wax warmer 300 includes enhanced retention of the electrical cord in the circumstance that the wax warmer is damaged, exposing the internal components.

Turning now to FIGS. 10-14, the wax warmer 300 is designed to heat a wax melt 302 and thereby release a fragrance or other material contained therein into the surrounding environment. The wax warmer 300 generally includes a body 304, a reservoir 306, and a heater assembly 308 (see FIG. 24). The body 304 is fashioned to house the heater assembly 308 and provide a support structure for the reservoir 306. The wax warmer 300 is generally described to include the aforementioned components, but the wax warmer 300 may be adapted to add or remove various components according to specific user requirements.

Figure 10:
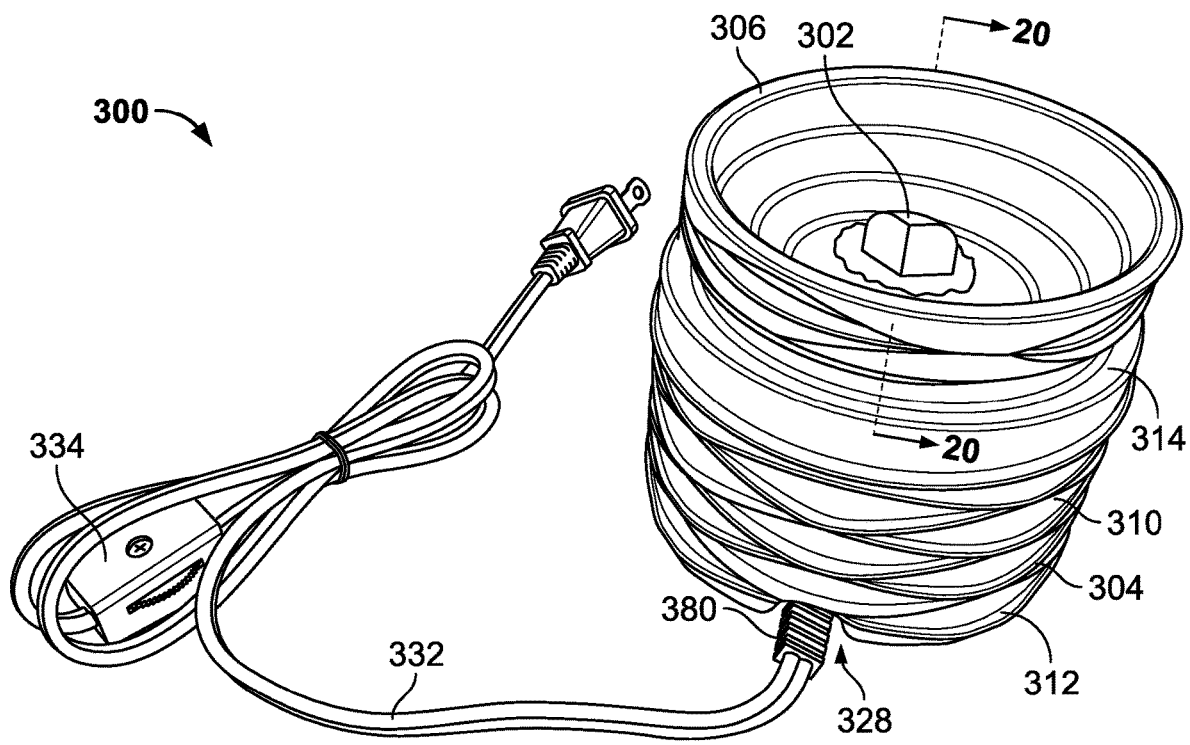
FIG. 10 is perspective view of another embodiment of a wax warmer.
Figure 11:
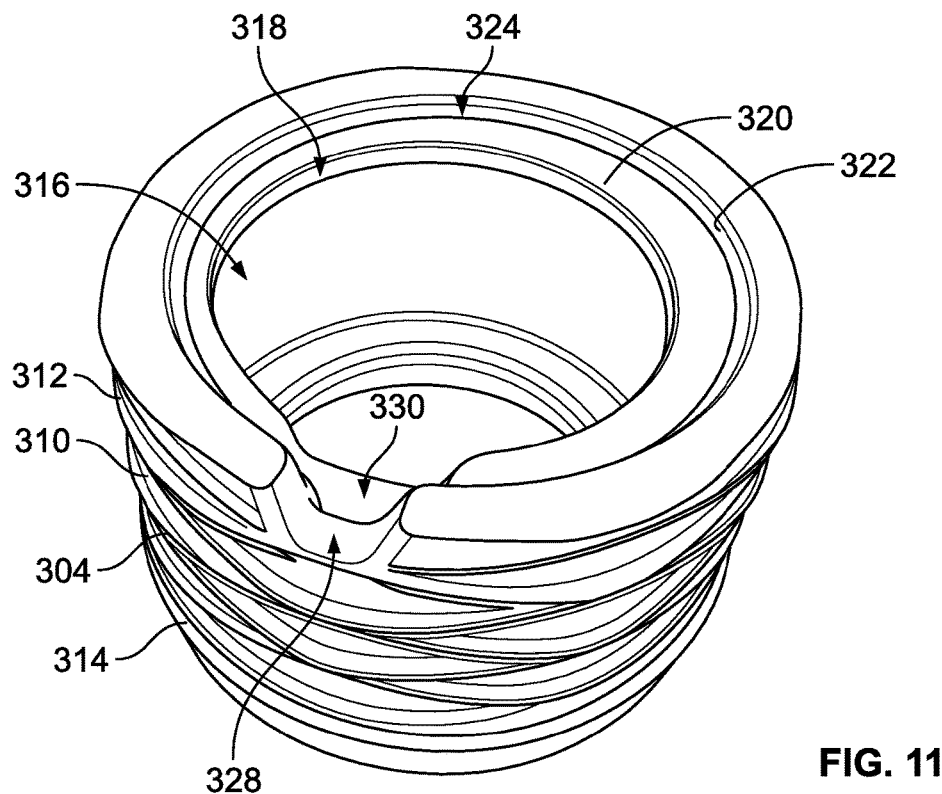
FIG. 11 is perspective view of a bottom end of a body of the wax warmer of FIG. 10.
Figure 12:
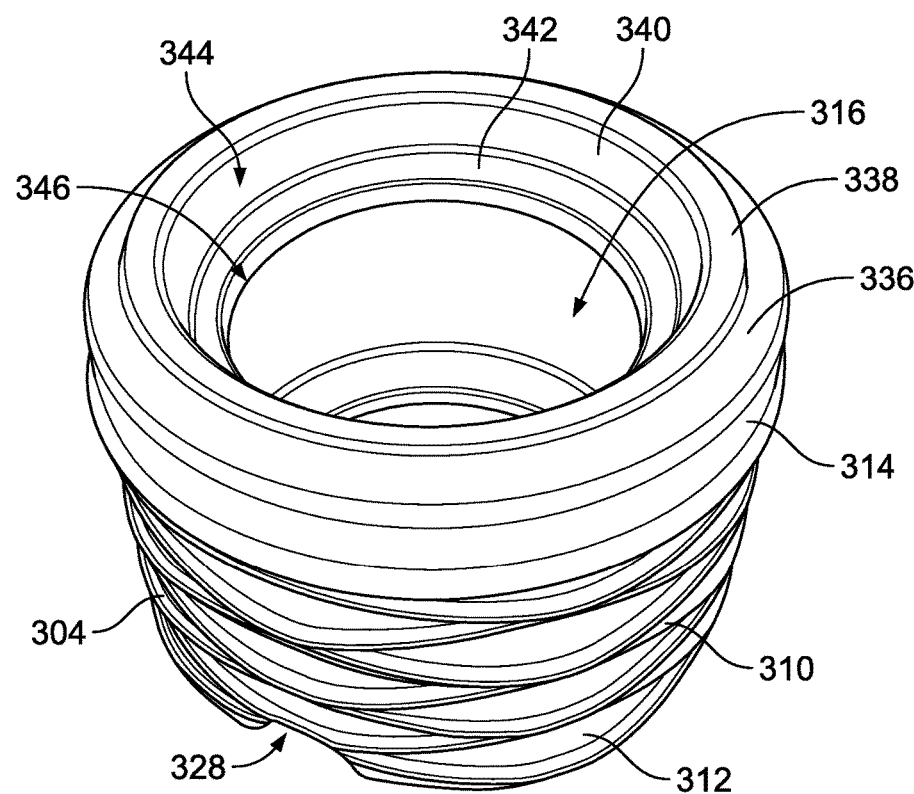
FIG. 12 is a perspective view of a top end of the body of the wax warmer of FIG. 10.
Figure 13:
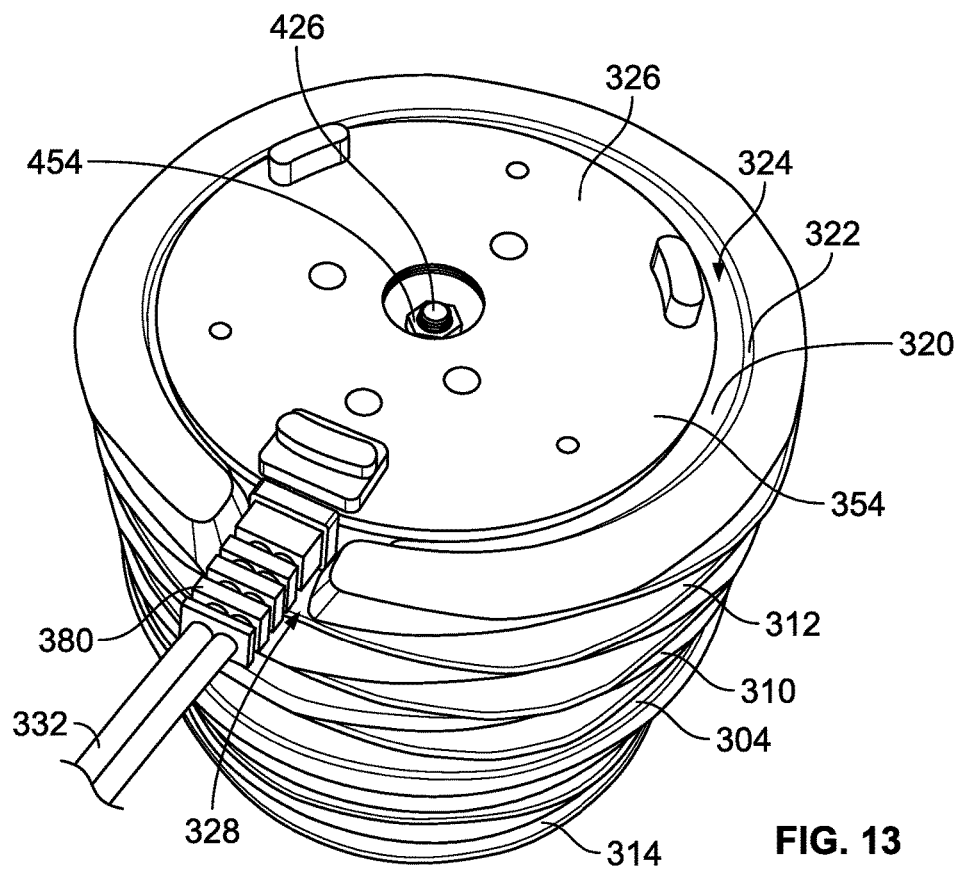
FIG. 13 is a perspective view of the bottom end of the assembled wax warmer of FIG. 10.
Figure 14:
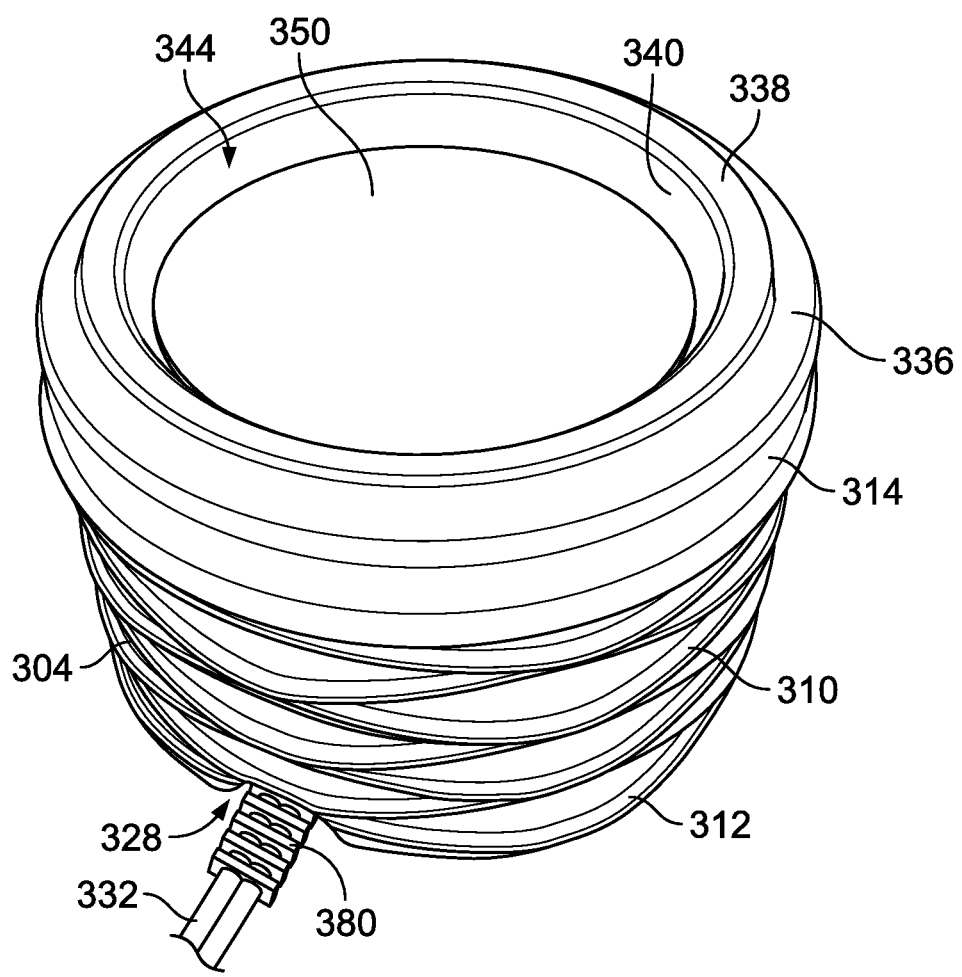
FIG. 14 is a perspective view of the top end of the wax warmer of FIG. 10 with the reservoir removed exposing a heater plate.

Referring now to FIGS. 10-12, the body 304 includes a side wall 310 having a bottom end 312 and a top end 314. In the present embodiment, the side wall 310 is generally cylindrical in shape and defines an interior space 316. The bottom end 312 defines a first opening 318. A recessed first lip 320 extends from an inner surface 322 of the side wall 310. The bottom end 312 and the first lip 320 form a bottom recess 324 adapted to receive a base plate 326 (see FIG. 13) that is disposed adjacent the bottom end 312 of the body 304. A cable aperture 328 is defined by and formed in the bottom end 312 of the side wall 310. The cable aperture 328 includes an inner recessed portion 330 (see FIG. 11) formed by a portion of the first lip 320. The wax warmer 300 further includes an electrical cord 332 (see FIG. 13) that is configured to be connected to a household electrical outlet (not shown) to provide electrical current to the heater assembly 308. The electrical cord 332 includes a switch 334 (see FIG. 10) for selectively activating the heater assembly 308.

Turning now to FIG. 12, the top end 314 of the body 304 includes a top shoulder 336 and an upper lip 338 disposed radially inwardly from, and extending upwardly from, the top shoulder 336. The upper lip 338 includes an inner wall 340 that extends downwardly into the interior space 316 of the body 304 and terminates at a heater plate lip 342 that extends inwardly from the inner wall 340. The inner wall 340 of the upper lip 338 and the heater plate lip 342 define a top recess 344. The heater plate lip 342 defines a second opening 346 from the top recess 344 into the interior space 316 of the body 304. The top recess 344 is configured to removably receive the reservoir 306. A heater plate 350 is sized to be positioned in the top recess 344 and cover the second opening 346 (see FIG. 14). The heater plate 350 supports the reservoir 306 when the reservoir 306 is positioned in the top recess 344.

Figures 15, 16:
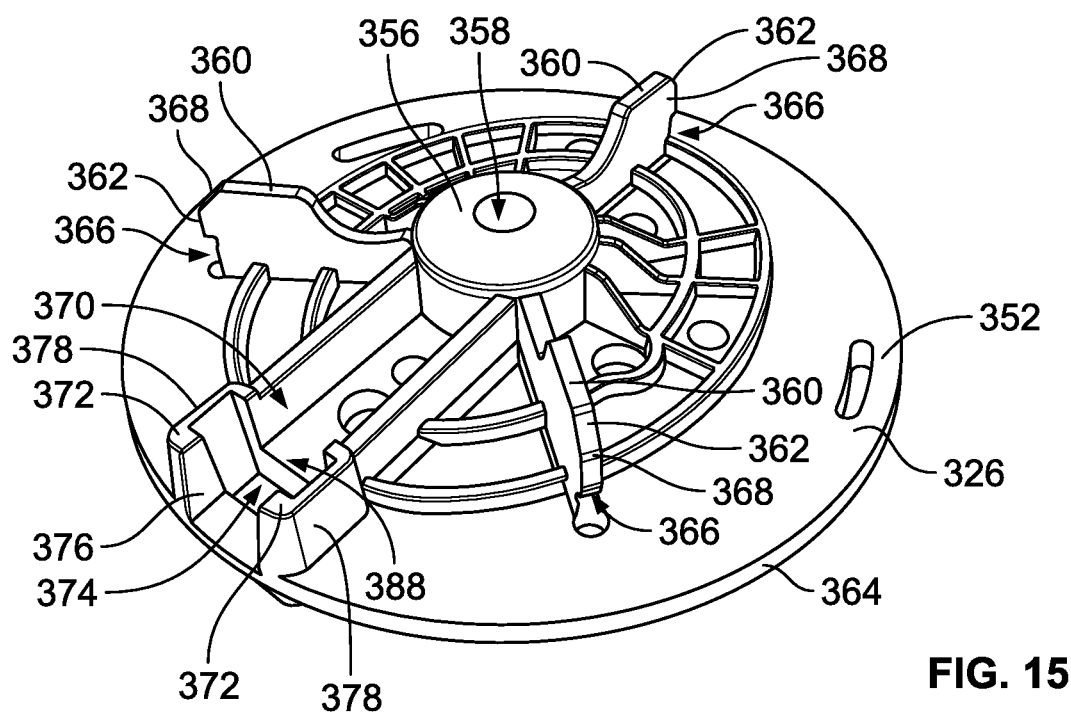
FIG. 15 is a perspective view of a base plate of the wax warmer of FIG. 10.
FIG. 16 is a perspective view of the base plate of FIG. 15 assembled with a portion of an electrical cord.

Referring now to FIGS. 15 and 16, the base plate 326 is depicted removed from the body 304. The base plate includes an upper side 352 and a lower side 354 (see FIG. 13). When the base plate 326 is positioned in the bottom recess 324 the upper side 352 faces the interior space 316 of the body 304. A central projection 356 extends upwardly from the upper side 352 and defines a central aperture 358. A plurality of fins 360 extend upwardly from the upper side 352 and radially outward from the central projection 356. In the present embodiment there are three fins 360 depicted. However, it is contemplated that more or fewer fins 360 may be present. Each of the plurality of fins 360 includes an outer end 362 that is spaced apart and radially inward from an edge 364 of the base plate 326. The outer end 362 of each fin 360 defines a recessed notch 366, which forms a protrusion 368 on the outer end 362 above the recessed notch 366.

Still referring to FIGS. 15 and 16, the base plate 326 also includes a cord retention channel 370, which is defined by two walls 372 that extend upwardly from the upper side 352 of the base plate 326. The two walls 372 also extend from the central projection 356 to the edge 364 of the base plate 326. The two walls 372 are offset from the central aperture 358 and are generally parallel to each other. The cord retention channel 370 includes a U-shaped recessed portion 374 that is defined by the inner surfaces 376 of the walls 372 and a portion of the upper side 352 of the base plate 326 within the cord retention channel 370. An end portion 378 of the walls 372 that is formed around the U-shaped recessed portion 374 is sized and positioned to fit inside the inner recessed portion 330 of the cable aperture 328 when the base plate 326 is placed within the bottom recess 324 of the body 304.

Turning now to FIG. 16, a portion of the electrical cord 332 that passes through the cable aperture 328 and into the interior space 316 to connect with the heater assembly 308 (see FIG. 24) when the wax warmer 300 is assembled is depicted assembled with the base plate 326. The electrical cord 332 includes a strain relief section 380 that comprises a series of molded sections that are configured to reduce the flexibility of that portion of the electrical cord 332 to prevent damage to the conductors inside. Positioned adjacent to the strain relief section 380 is a retention flange 382, which is sized to be positioned within the U-shaped recess 374 of the cord retention channel 370. After the retention flange 382, the electrical cord 332 comprises two separate insulated conductors 384 that are twisted into a knot 386 and continue on to connect to the heater assembly 308. It is contemplated that the knot 386 may serve multiple functions. First, the knot 386 may provide strain relieve on the connection of the cord 332 to the heater assembly 308 during assembly of the wax warmer 300. Second, the knot 386 may serve as a secondary retention feature, the details of which will be disclosed later.

Figure 17:
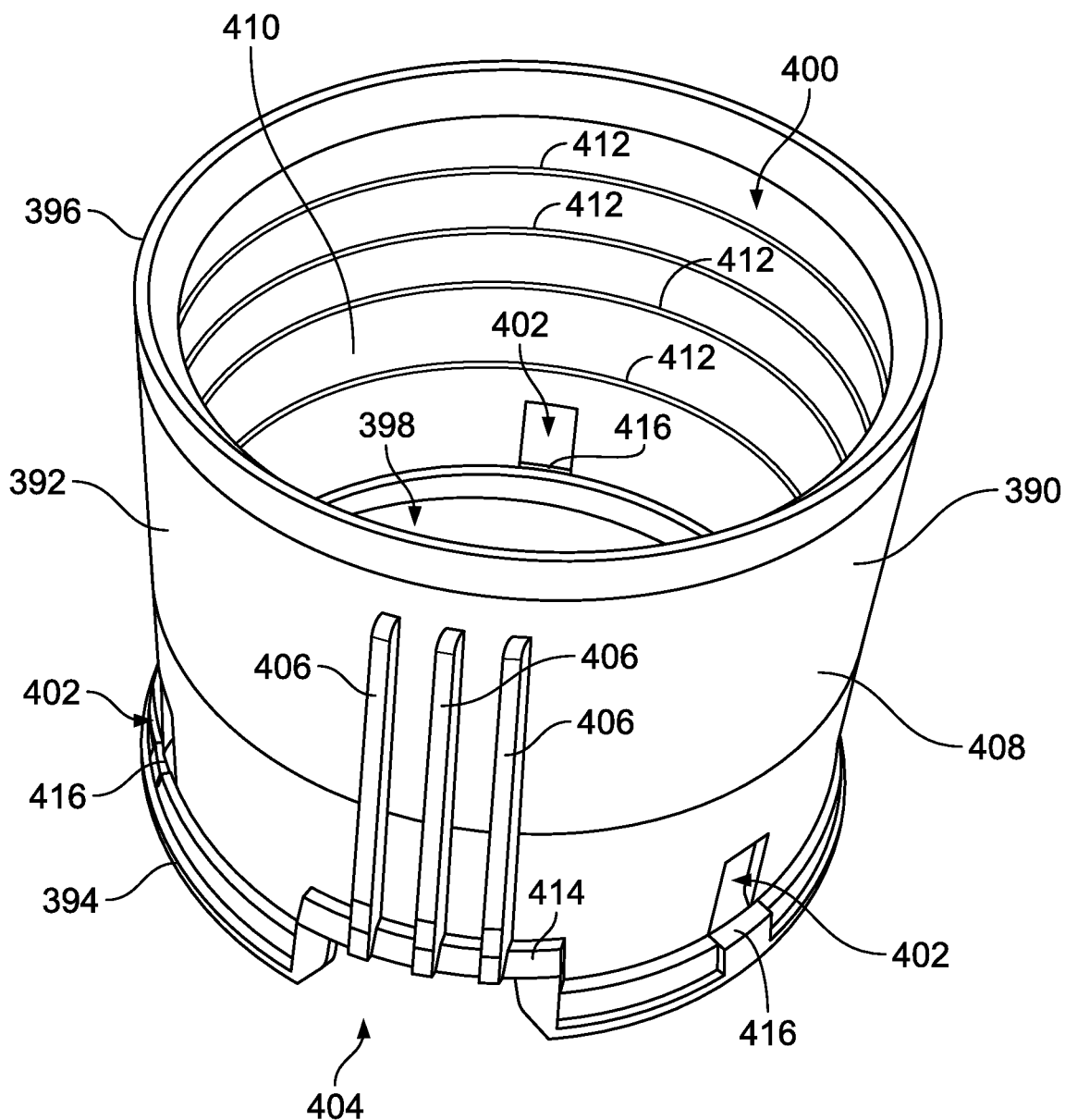
FIG. 17 is a front perspective view of a sleeve that forms an electrical barrier of the wax warmer of FIG. 10.
Figure 18:
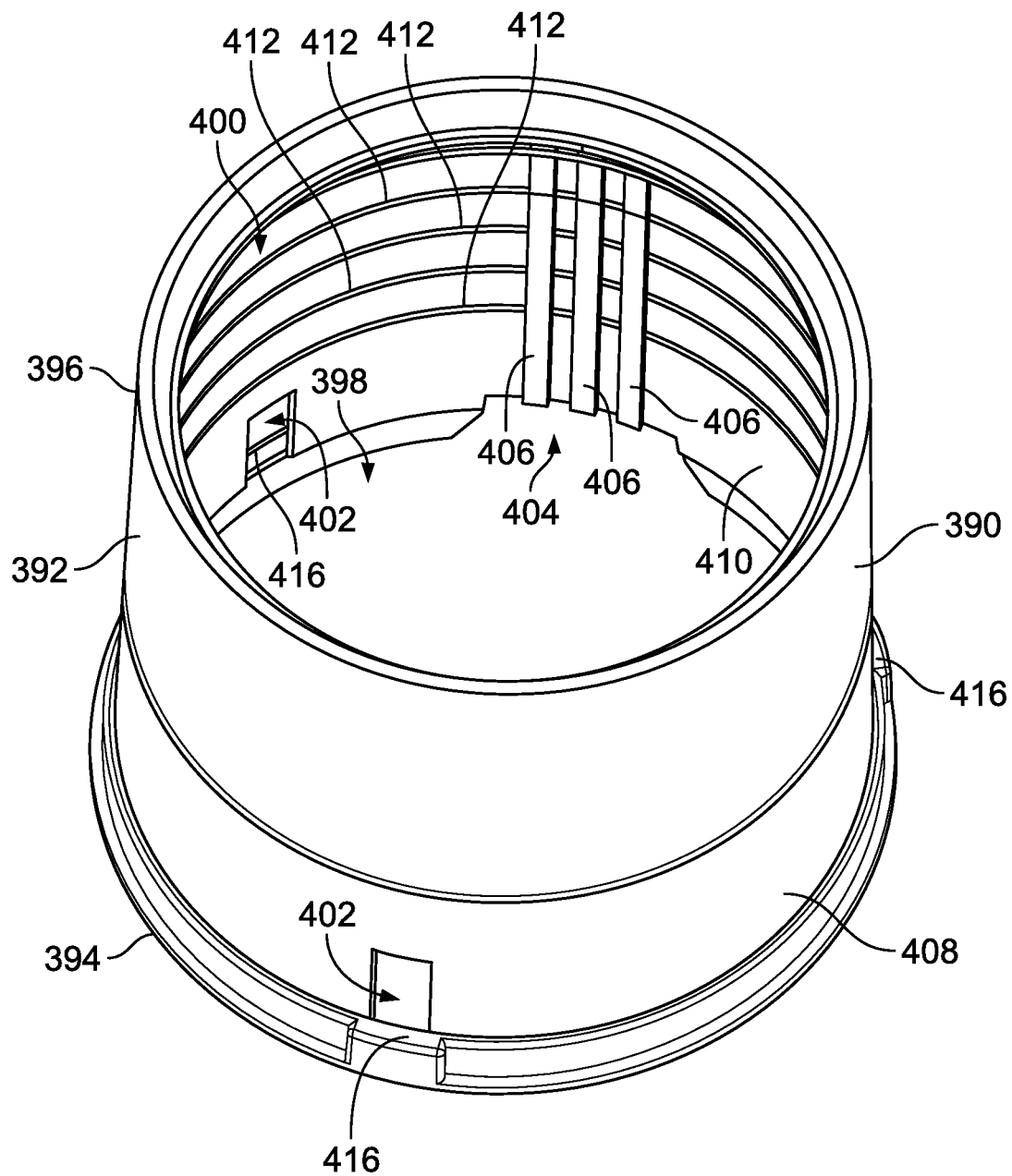
FIG. 18 is a rear perspective view of the sleeve of FIG. 17.

Turning now to FIGS. 17 and 18, an embodiment of a sleeve 390 that is configured to couple to the base plate 326 (see FIG. 19) and form an electrical barrier within the interior space 316 is depicted. The sleeve 390 generally comprises a cylindrical side wall 392 and is formed from a rigid and non-conductive material. The side wall 392 includes a bottom end 394 and a top end 396. The bottom end 394 defines a bottom opening 398, and the top end 396 defines a top opening 400. The side wall 392 further defines a plurality of retention apertures 402 that are spaced around the circumference of the side wall 392 and proximate the bottom end 394. The side wall 392 also defines a cord aperture 404 and a plurality of vertical ribs 406 that begin proximate the top end 396 of the sleeve 390 and terminate at the cord aperture 404. The vertical ribs 406 extend outwardly from an outer surface 408 of the side wall 392 and inwardly from an inner surface 410 of the side wall 392. The inner surface 410 also includes a plurality of inwardly protruding horizontal ribs 412 that are spaced apart vertically between the retention apertures 402 and the top end 396 of the side wall 392. The vertical ribs 406 and the horizontal ribs 412 strengthen the side wall 392 to reduce the possibility of the sleeve 390 failing in the event of an impact to the body 304. The cord aperture 404 also includes a protruding lip 414 that reinforces and strengthens the portion of the side wall 392 around the cord aperture 404. It is contemplated that when the sleeve 390 is coupled to the base plate 326 (see FIG. 19) all of the electrical components of the wax warmer 300 that are within the interior space 316 will be surrounded by the sleeve 390. That is, the sleeve 390 will form an electrical barrier should the body 304 be damaged as described earlier.

Figure 19:
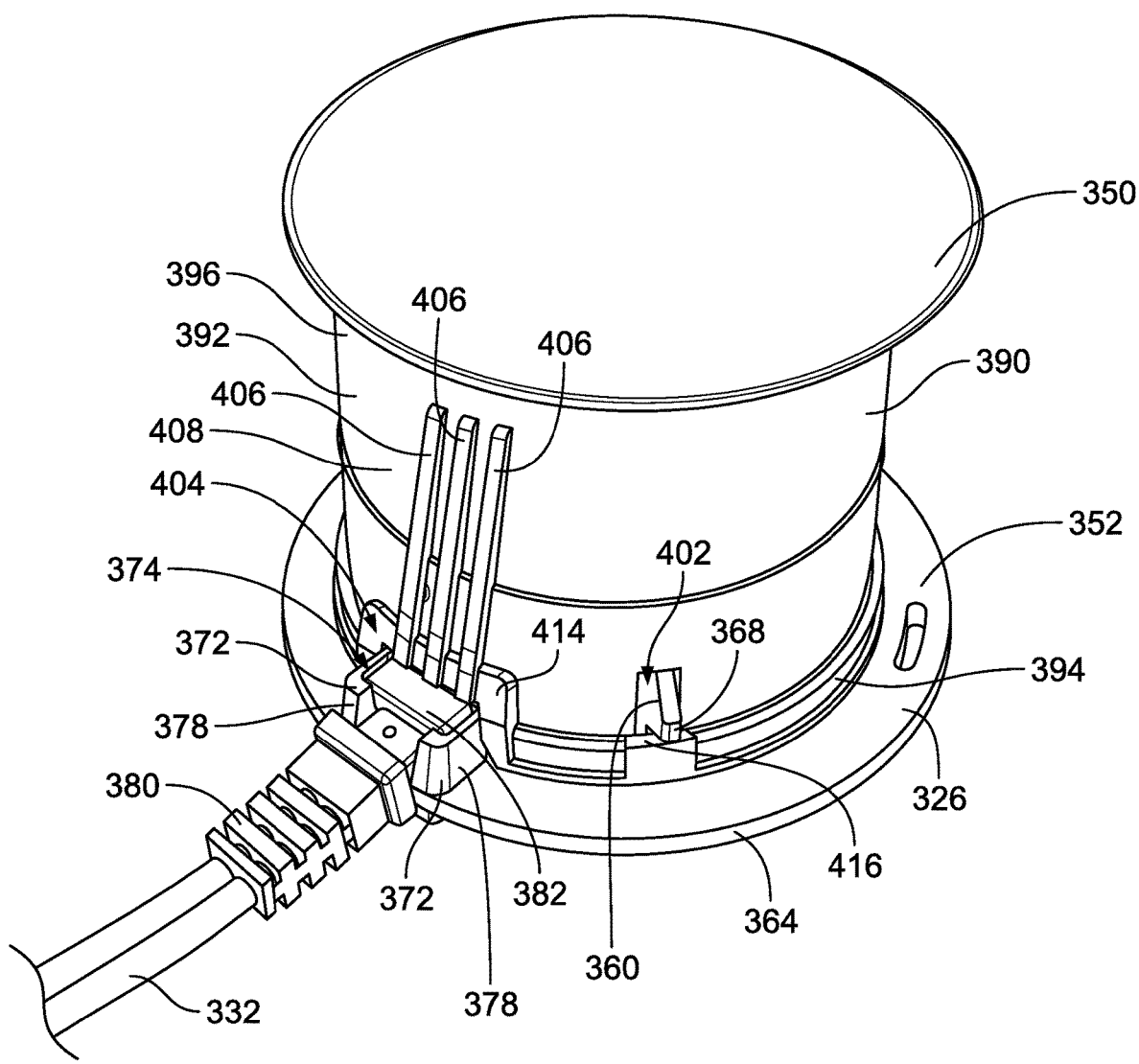
FIG. 19 is a perspective view of the sleeve of FIG. 17 assembled with the base plate and electrical cord of FIG. 16 and the heater plate of FIG. 14.

Turning now to FIG. 19, the sleeve 390 is depicted assembled and coupled to the base plate 326 at the bottom end 394 of the sleeve 390, and the heater plate 350 positioned on the top end 396 of the sleeve 390. When the sleeve 390 is coupled to the base plate 326, the cord aperture 404 is positioned to fit around the cord retention channel 370 adjacent to a portion of the U-shaped recessed portion 374. The sleeve 390 is coupled to the base plate 326 by the protrusions 368 of the plurality of fins 360 extending through the plurality of retention apertures 402. The protrusions 368 are spaced apart from the upper side 352 of the base plate 326 by the height of the recessed notches 366 (see FIG. 16). The height of the recessed notches 366 is sized so that the protrusions 368 are positioned over a bottom edge 416 of the retention apertures 402, thereby providing a secure fit between the base plate 326 and the sleeve 390. The coupling of the sleeve 390 to the base plate 326 retains the electrical cord 332 within the cord retention channel 370.

As depicted in FIG. 19, the retention flange 382 of the electrical cord 332 is positioned within the U-shaped recessed portion 374. The perimeter of the cord aperture 404 is sized to provide a snug fit about an end portion 388 (see FIG. 16) of the U-shaped recess portion 374. Further, as can been seen in FIGS. 19 and 20, the protruding lip 414 and the protruding portions of the vertical ribs 406 extend above the retention flange 382 of the electrical cord 332. Thus, in the event that the body 304 surrounding the sleeve 390 is damaged so that the portion of side wall 310 that defines the cable aperture 328 is removed, the electrical cord 332 is retained at least partially within the U-shaped recess portion 374 of the cord retention channel 370. The protruding lip 414 and the vertical ribs 406 lock the retention flange 382 in place or at least significantly restrict any movement of the retention flange 382 relative to the sleeve 390, in order to prevent the retention flange 382 from being withdrawn from the U-shaped recess portion 374. By retaining the electrical cord 332 in this way, the electrical components of the wax warmer 300 are locked inside the sleeve 390 and do not present an electric shock risk to a user trying to recover a broken device. Further, if the retention flange 382 was somehow displaced from the U-shaped recessed portion 374, the knot 386 (see FIG. 16) formed by the insulated conductors 384 is positioned inside of the sleeve 390 and is substantially larger than the space between the walls 372 that form the cord retention channel 370 and the perimeter of the cord aperture 404. Pulling on the cord 332 hard enough to force the knot 386 through the opening defined by the U-shaped recess portion 374 and the cord aperture 404 would require a significant amount of force that would most likely result in the material failure of the sleeve 390 and/or the base plate 326. Thus, under circumstances that the body 304 is damaged and the retention flange 382 is displaced, the electrical cord 332 would thereby still be prevented from pulling out of the sleeve 390 and exposing any energized electrical components of the wax warmer 300. Note, the knot 386 has been removed from FIG. 20 for clarity so as to avoid obscuring other elements.

Figure 20:
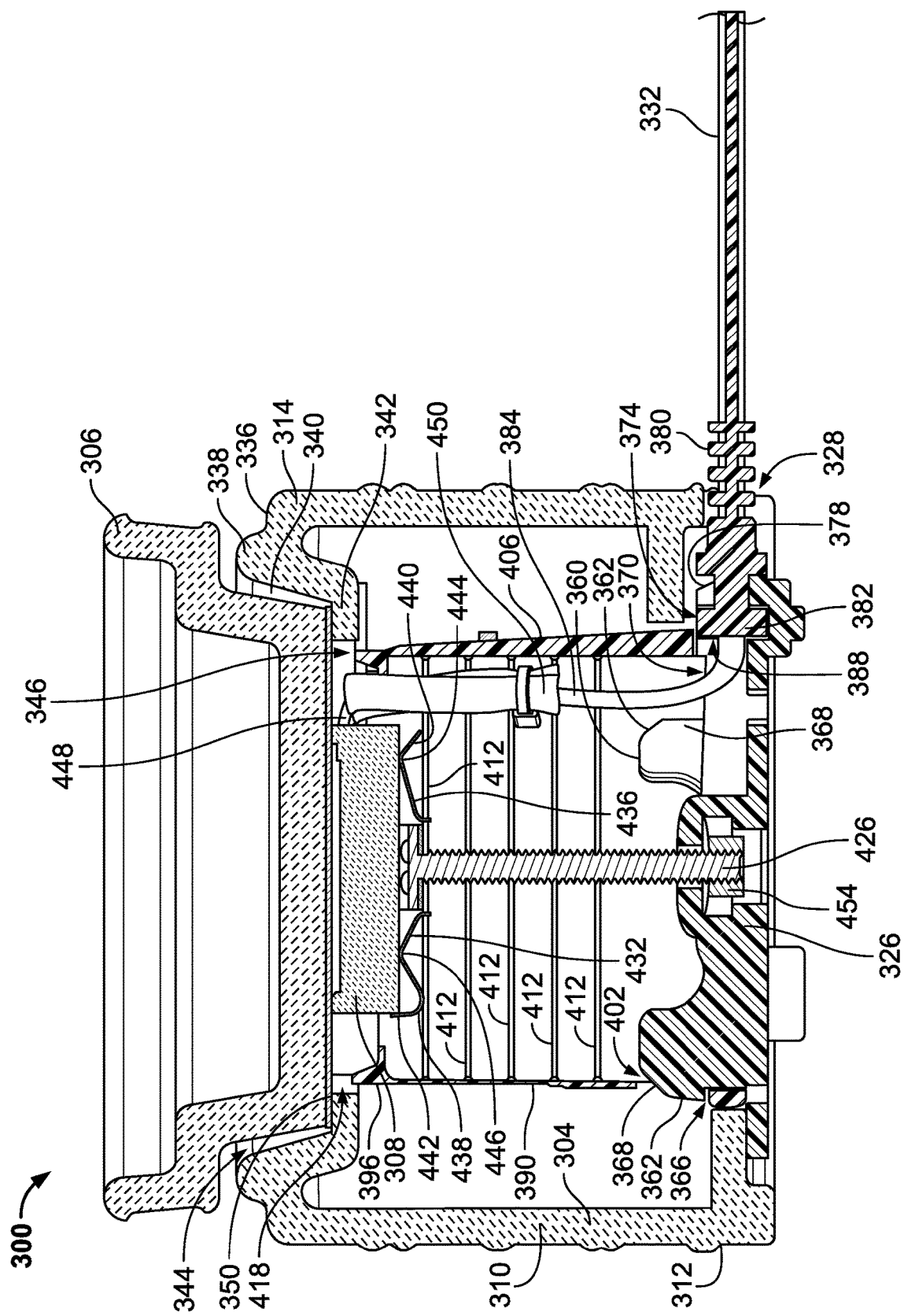
FIG. 20 is a cross section of the wax warmer of FIG. 10 taken along the line 20-20 shown in FIG. 10.
Figure 21:
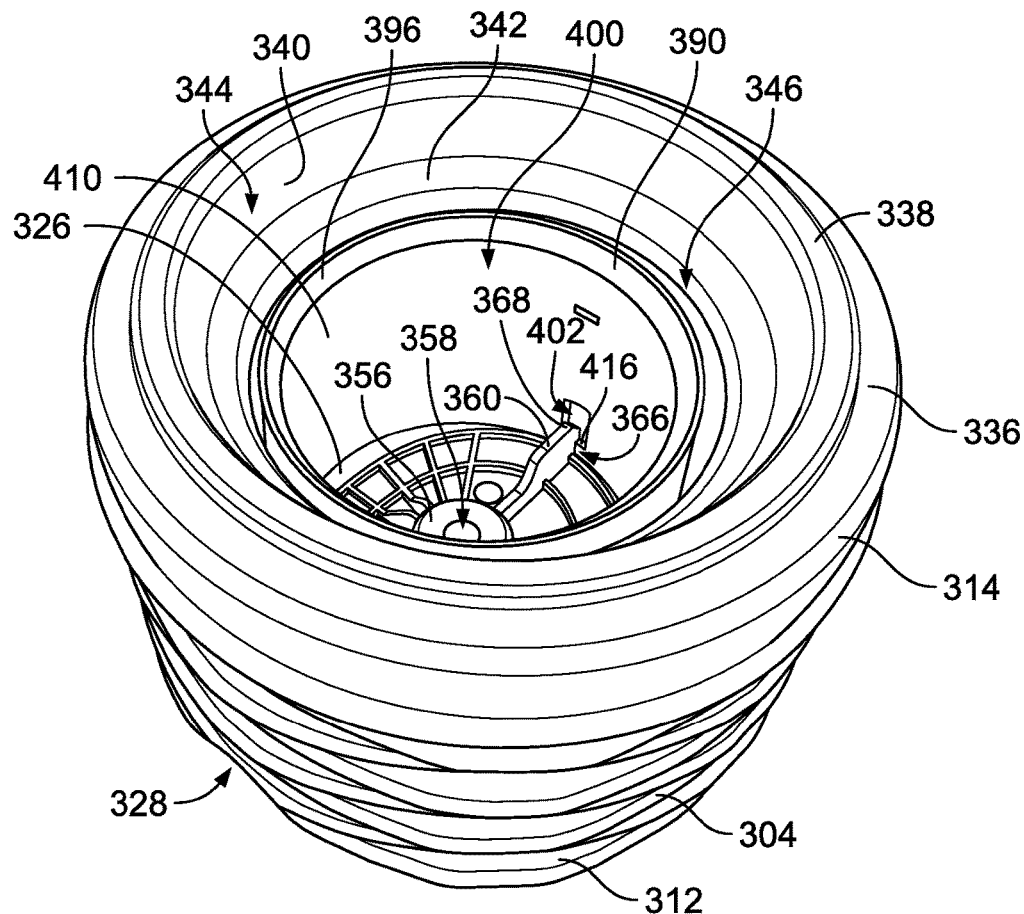
FIG. 21 is a perspective view of the body of the wax warmer of FIG. 10 assembled with the base plate and the sleeve.

Turning now to FIG. 20, a cross section of the wax warmer 300 taken along the line 20-20 of FIG. 10 is depicted. A gap 418 is formed between the heater plate 350 and the top end 396 of the sleeve 390. It is contemplated that in some embodiments the top end 396 of the sleeve 390 may contact the heater plate 350. In the event that the body 304 is damaged, and at least a portion of the body 304 is removed, the gap 418 is sized to prevent a user from contacting a live electrical component within the sleeve 390. The upper end 396 of the sleeve 390 is positioned within the second opening 346 of the body 304 and adjacent the heater plate lip 342. The upper end 396 of the sleeve 390 substantially fills the second opening 346 (as seen, e.g., in FIG. 21). When the heater plate 350 is assembled to the device, the top end 396 of the sleeve 390 is adjacent and in close proximity to the heater plate 350.

Figure 22:
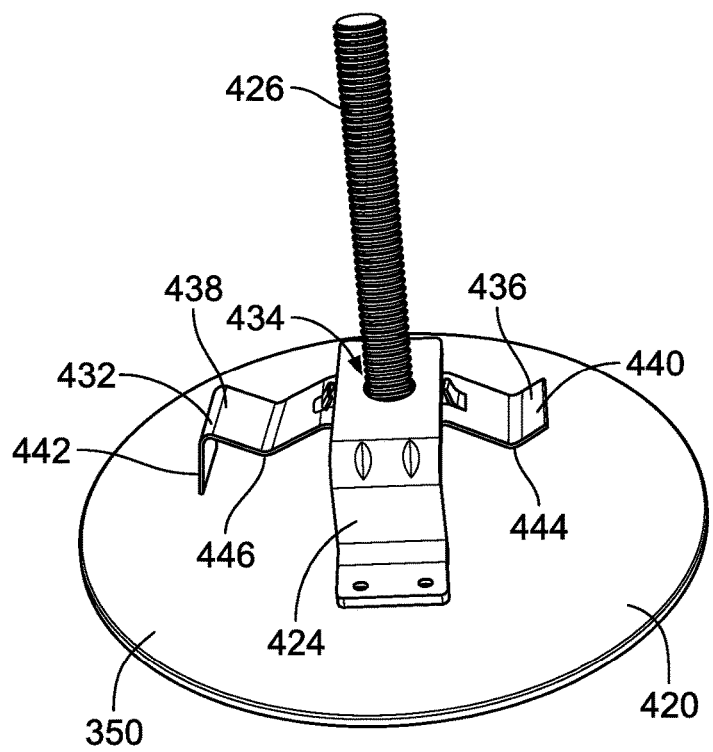
FIG. 22 is a perspective view of the bottom of the heater plate of the wax warmer of FIG. 10.
Figure 23:
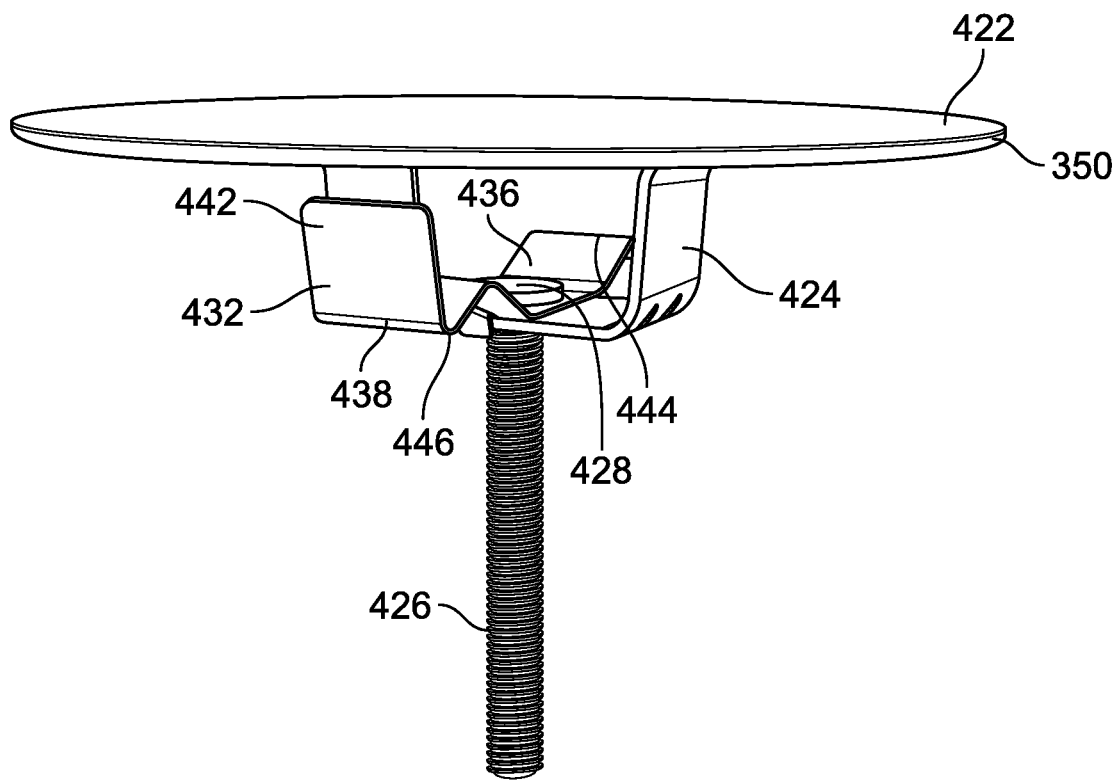
FIG. 23 is another perspective view of the heater plate of FIG. 22.
Figure 24:
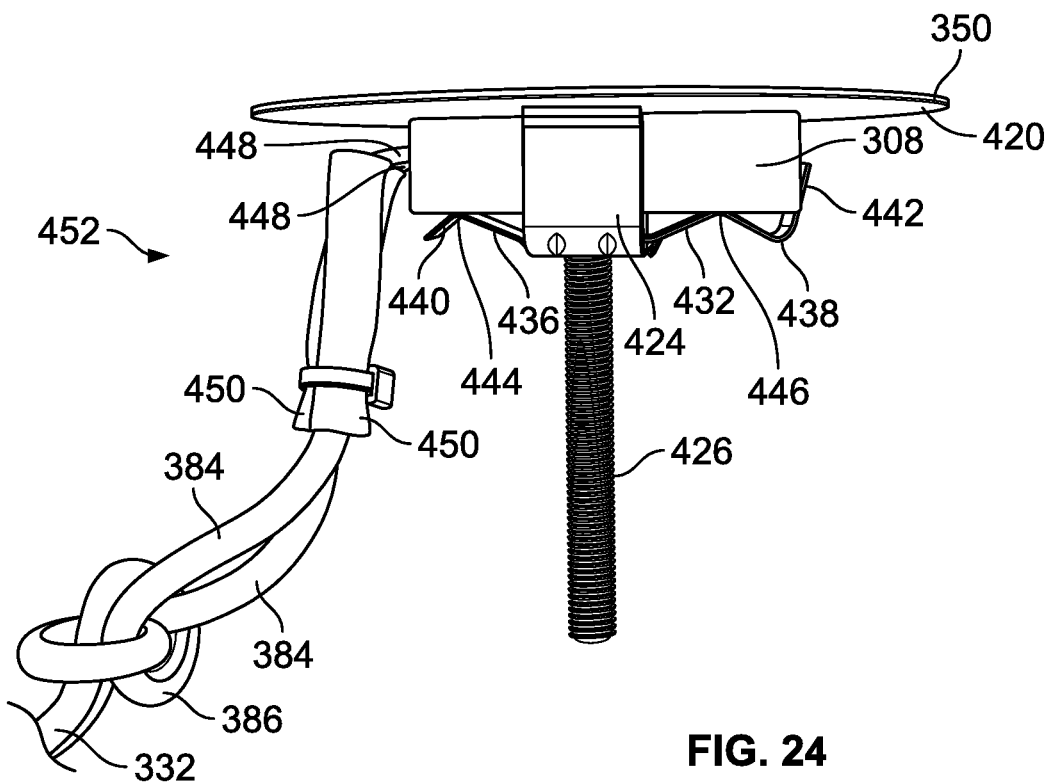
FIG. 24 is a side elevational view of the heater plate of FIG. 22 depicting the heater assembly installed and retained in contact with the heater plate.

Turning now to FIGS. 22-24, the heater plate 350 and heater assembly 308 retention features are depicted. The heater plate 350 includes a bottom surface 420 and a top surface 422. A retention bracket 424 extends from the bottom surface 420 of the heater plate 350. A threaded rod 426 includes a flat head 428. The threaded rod 426 extends through an aperture (not shown) defined by a resilient heater retainer clip 432 and an aperture 434 defined by the retention bracket 424. The aperture (not shown) defined by the resilient heater retainer clip 432 is covered by the flat head 428 as depicted in FIG. 23. The resilient heater retainer clip 432 includes a first end 436 and a second end 438. A first flap 440 is formed in the first end 436 of the resilient heater retainer clip 432 and a second flap 442 is formed in the second end 438. The first flap 440 extends away from the bottom surface 420 of the heater plate 350. The second flap 442 extends toward the bottom surface 420 of the heater plate 350. Between the aperture (not shown) and the first end 436 and second end 438, the resilient heater clip 432 diverges toward and then away from the bottom surface 420 of the heater plate 250, thereby forming a first clamp portion 444 and a second clamp portion 446. A distance between the bottom surface 420 of the heater plate 350 and one or both of the first clamp portion 444 and the second clamp portion 446 is less than or equal to a thickness of the heater assembly 308, in order to effectuate a clamping force on the heater assembly, as depicted in FIG. 24. The heater assembly 308 is positioned between the heater plate 350 and the resilient heater retainer clip 432, which secures the heater assembly 308 in contact with the bottom surface 420 of the heater plate 350. When installed, the heater assembly 308 extends through and is positioned within the retention bracket 424. The resilient heater retainer clip 432 is positioned between the heater assembly 308 and the retention bracket 424.

Still referring to FIG. 24, the heater assembly 308 includes two insulated electrical leads 448 that are connected to the insulated conductors 384 of the electrical cord 332. Metallic electrical conductors (not shown) inside the electrical leads 448 are in electrical communication with metallic electrical conductors (not shown) inside the insulated conductors 384 of the electrical cord 332. The electrical connections are made within insulating sleeves 450 to prevent any short circuits. The wax warmer 300 may include an electrical assembly 452 that comprises the heater assembly 308 and the portion of the electrical cord 332 that is positioned within the sleeve 390. It is contemplated that the electrical assembly 452 may include other electrical or electronic components. However, it is also contemplated that any and all electrical or electronic components that may be included in the electrical assembly 452 are positioned within the sleeve 390 to prevent any chance of exposure if the body 304 is damaged or broken.

A non-limiting example of how the wax warmer 300 may be assembled is described below. The heater assembly 308 is positioned within the retention bracket 424 by sliding it between the bottom surface 420 and the resilient heater retainer clip 432. The electrical cord 332 is then passed through the body 304 until the heater plate 350 is positioned on the heater plate lip 342 with the threaded rod 426 extending through the interior space 316 of the body 304. The electrical cord 332 is then passed through the sleeve 390 until the sleeve 390 is positioned within the interior space 316 and the cord aperture 404 is aligned with the cable aperture 328 of the body. The retention flange 382 of the electrical cord 332 is then inserted into the U-shaped recessed portion 374 of the cord retention channel 370. The base plate 326 with the electrical cord 332 installed in the cord retention channel 370 is then coupled to the sleeve 390. When the base plate 326 is coupled to the sleeve 390 the threaded rod 426 extends through the interior space 316 and into the central aperture 358. When the base plate 326 is positioned within the bottom recess 324, the strain relief section 380 is aligned with the cable aperture 328 of the body 304. The heater plate 350 rests on the heater plate lip 342 and the base plate 326 is positioned against the first lip 320. A nut 454 may be threaded onto the exposed end of the threaded rod 426 (see FIGS. 13 & 20) to provide tension in the threaded rod 426 to maintain the heater plate 350 and the base plate 326 in position. When assembled, the sleeve 390 surrounds the electrical assembly 452 within the body 304 and performs as a rigid electrical barrier if the body 304 is broken.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmer that utilizes wax melts or the like.

INDUSTRIAL APPLICABILITY

A wax warmer is presented that provides an electrical barrier. Thus, a user may be inhibited from contacting live electrical components in the event that the wax warmer is damaged.

Numerous modifications to the present invention will be apparent to those skilled in the art in view of the foregoing description. Accordingly, this description is to be construed as illustrative only and is presented for the purpose of

We claim:

1. A wax warmer, comprising:
   a body;
   an electrical assembly positioned within an interior space of the body and including an electrical cord that extends outside the body;
   a base plate having at least one fin; and
   a sleeve forming an electrical barrier positioned within the interior space and surrounding the electrical assembly, the sleeve having at least one aperture,
   wherein the sleeve is coupled to the base plate by a portion of the at least one fin extending into the at least one aperture of the sleeve, and
   wherein a portion of the electrical cord that passes through an opening in the sleeve is retained by the base plate and the sleeve.

2. The wax warmer of claim 1, wherein the base plate includes a cord retention channel having a recessed portion.

3. The wax warmer of claim 2, wherein the electrical cord includes a retention flange sized to be positioned within the recessed portion of the cord retention channel.

4. The wax warmer of claim 3, wherein the retention flange of the electrical cord is retained at least partially within the recessed portion of the cord retention channel by at least one of a portion of a protruding lip and a rib.

5. The wax warmer of claim 1, wherein the interior space is defined between a heater plate, the base plate, and the body.

6. The wax warmer of claim 5, wherein the sleeve extends from the base plate to adjacent the heater plate.

7. A wax warmer, comprising:
   a body;
   an electrical assembly positioned within an interior space of the body;
   an electrical cord that couples to the electrical assembly; and
   an annular sleeve positioned within the interior space of the body, wherein the annular sleeve surrounds the entire electrical assembly and securely retains a portion of the electrical cord within the body.

8. The wax warmer of claim 7 further including a base plate and a top plate, wherein the annular sleeve extends from the base plate to adjacent the top plate.

9. The wax warmer of claim 8, wherein the annular sleeve is coupled to the base plate.

10. The wax warmer of claim 7 further including a base plate, wherein the annular sleeve is coupled to the base plate, and wherein the electrical cord passes through an opening defined by the annular sleeve and a portion of the baseplate.

11. The wax warmer of claim 10, wherein a portion of the electrical cord is retained at least partially within the opening defined by a portion of the base plate and the annular sleeve.

12. The wax warmer of claim 11, wherein the base plate includes at least one fin and the annular sleeve includes at least one aperture, and wherein the annular sleeve is coupled to the base plate by a portion of the at least one fin extending through the at least one aperture.

13. A wax warmer, comprising:
    a body including a top plate and a base plate;
    a reservoir positioned on the top plate of the body;
    an electrical assembly positioned within an interior space of the body; and
    an annular sleeve coupled to the base plate and forming an electrical barrier,
    wherein the annular sleeve is positioned within the interior space and surrounds the electrical assembly within the body;
    wherein the electrical assembly includes a heater in thermal contact with the top plate.

14. The wax warmer of claim 13, wherein the heater is retained in contact with the top plate by a resilient clip.

15. The wax warmer of claim 14, wherein the heater and the resilient clip are positioned within a bracket extending from the top plate, and wherein the heater is retained in contact with the top plate by the resilient clip positioned between the heater and the bracket.

16. The wax warmer of claim 15 further including an electrical cord that is coupled to the electrical assembly and passes through an opening defined by the annular sleeve and a portion of the base plate, wherein at least a portion of the electrical cord is retained within a recess of the base plate by the annular sleeve.

* * * * *